(12) United States Patent
Price et al.

(10) Patent No.: US 12,245,589 B2
(45) Date of Patent: Mar. 11, 2025

(54) OMEGA-ALICYCLIC TUNICAMYCINS AND ANALOGS

(71) Applicant: The United States of America, as represented by the Secretary of Agriculture, Washington, DC (US)

(72) Inventors: Neil P. Price, Edelstein, IL (US);
Michael A. Jackson, Morton, IL (US);
Trina M. Hartman, Peoria, IL (US);
John P. Bannantine, Ames, IA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 108 days.

(21) Appl. No.: 17/718,981

(22) Filed: Apr. 12, 2022

(65) Prior Publication Data

US 2023/0320354 A1 Oct. 12, 2023

(51) Int. Cl.
*A01N 43/54* (2006.01)
*A01P 1/00* (2006.01)
*C07H 19/06* (2006.01)
*C12N 1/20* (2006.01)
*C12P 21/00* (2006.01)
*C12R 1/52* (2006.01)

(52) U.S. Cl.
CPC .............. *A01N 43/54* (2013.01); *A01P 1/00* (2021.08); *C07H 19/06* (2013.01); *C12N 1/20* (2013.01); *C12P 21/005* (2013.01); *C12R 2001/52* (2021.05)

(58) Field of Classification Search
CPC ........... A01N 43/54; A01P 1/00; C07H 19/06; C12N 1/20; C12P 21/005; C12R 2001/52
USPC ......................................................... 514/50
See application file for complete search history.

(56) References Cited

U.S. PATENT DOCUMENTS 10,513,533 B2 * 12/2019 Price ..................... A01N 43/16
2015/0175519 A1 6/2015 Sittiwong et al.
2018/0208620 A1 * 7/2018 Price .................. A61K 31/7034

OTHER PUBLICATIONS

Price et al., (2021), ACS Chem. Biol., vol. 16, Issue 1, p. 116-124 (Year: 2021).*
Labeda et al., (2016), J. Antibiot., vol. 69, p. 637-646 (Year: 2016).*
Labeda et al., Published May 18, 2016, J. Antibiot., vol. 69, pp. 637-646 (Year: 2016).*
Hering et al., Published Nov. 9, 2020, ACS Chemical Biology, vol. 15, pp. 2885-2895 (Year: 2020).*
BC Chung, 2013, "Crystal structure of MraY, an essential membrane enzyme for bacterial cell wall synthesis," Science 341 (6149): 1012-1016.
YY Dong, et al., 2018, "Structures of DPAGT1 Explain Glycosylation Disease Mechanisms and Advance TB Antibiotic Design," Cell 175(4):1045-1058.
JK Hakulinen, et al., 2017, "MraY-antibiotic complex reveals details of tunicamycin mode of action," Nat. Chem. Biol. 13 (3): 265-267.
J Hering, et al., 2018, "Structural basis for selective inhibition of antibacterial target MraY, a membrane-bound enzyme involved in peptidoglycan synthesis," Drug Discov. Today 23(7):1426-1435.
NPJ Price, et al., 2017, "Modified tunicamycins with reduced eukaryotic toxicity that enhance the antibacterial activity of lactams," J. Antibiot. 70 1070-1077.
NPJ Price, et al., 2019, "Synergistic enhancement of beta-lactam antibiotics by modified tunicamycin analogs TunR1 and TunR2," J. Antibiot. 72(11):807-815.
NPJ Price, et al., 2021, "Branched Chain Lipid Metabolism As a Determinant of the N Acyl Variation of Streptomyces Natural Products," ACS Chem. Biol. 16:116-124.
J Yoo, 2018, "GlcNAc-1-P-transferase-tunicamycin complex structure reveals basis for inhibition of N-glycosylation," Nat. Struct. Mol. Biol. 25(3): 217-224.

* cited by examiner

*Primary Examiner* — Yih-Horng Shihao
*Assistant Examiner* — Jaret J Crews
(74) *Attorney, Agent, or Firm* — John D. Fado; Maria Restrepo-Hartwig

(57) ABSTRACT

The invention relates to new tunicamycin structures comprising N-acyl groups metabolically integrated into the terminus of the TUN via the *Streptomyces* branched chain fatty acid pathways and variants thereof, and methods of preparing such new tunicamycin structures. The invention further relates to antibacterial compositions comprising such new tunicamycin structures, and methods for using such antibacterial compositions for killing Gram-positive bacteria.

10 Claims, 26 Drawing Sheets

Tunicamycin Tun-16:1-C5C

Tunicamycin Tun-14:1-C5C

Tunicamycin Tun-17:1-C6C

Tunicamycin Tun-15:1-C6C

Tunicamycin Tun-17:1-6C3ene

Tunicamycin Tun-15:1-6C3ene

Native tunicamycins from 12338

Tunicamycins from 12338 + C5C-primer

FIG. 9A       FIG. 9B       FIG. 9C
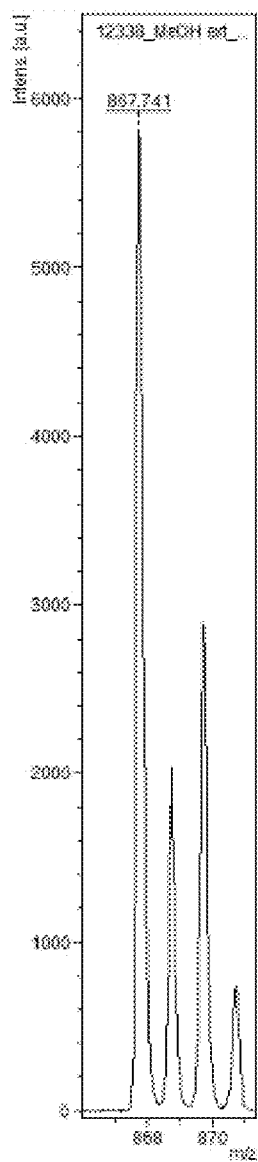
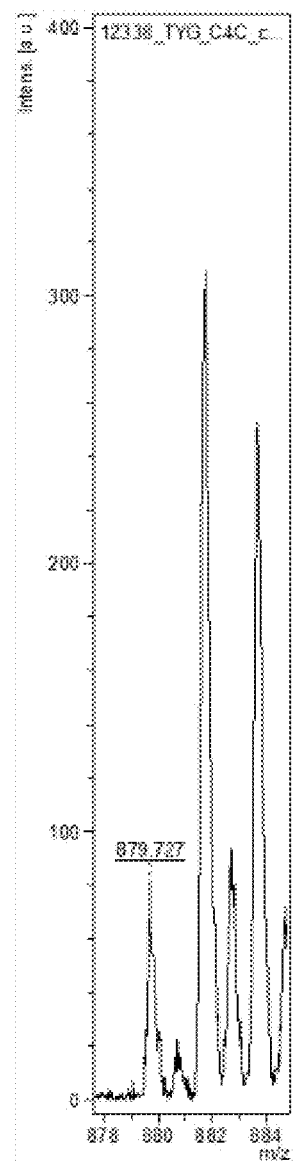
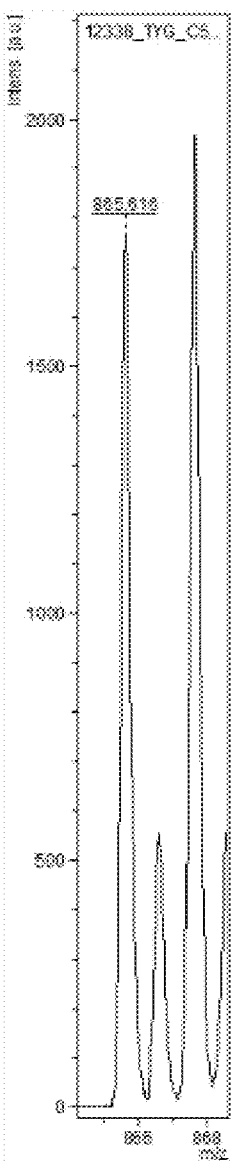
m/z 867　　　　　m/z 879　　　　　m/z 865
Tun16:1　　　　　Tun17:1-C4C　　　Tun16:1-C5C
Ratio　1.0　　　　　0.13　　　　　　0.90

FIG. 9D FIG. 9E FIG. 9F
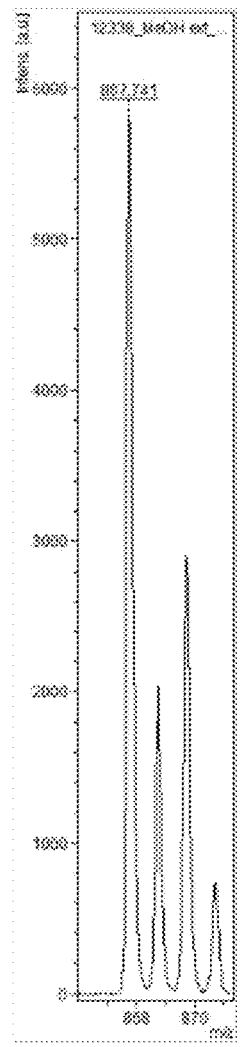
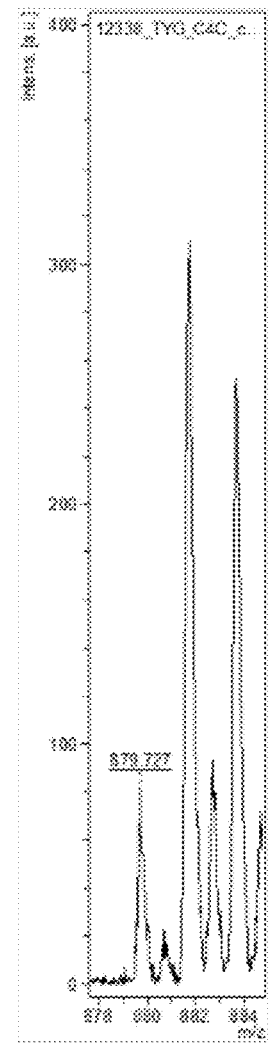
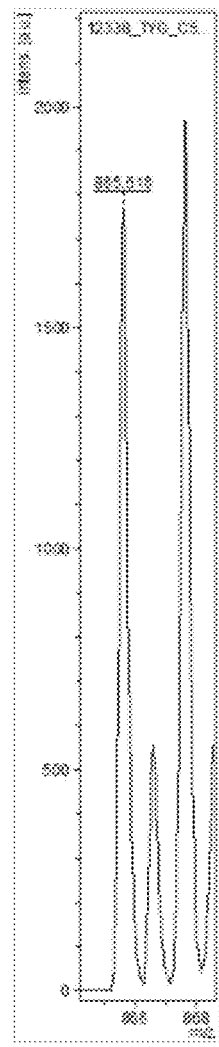
m/z 893
Tun18:1-C5C
0.42
m/z 879
Tun17:1-C6C
8.93
m/z 893
Tun18:1-C7C
0.11

FIG. 9G
FIG. 9H
FIG. 9I
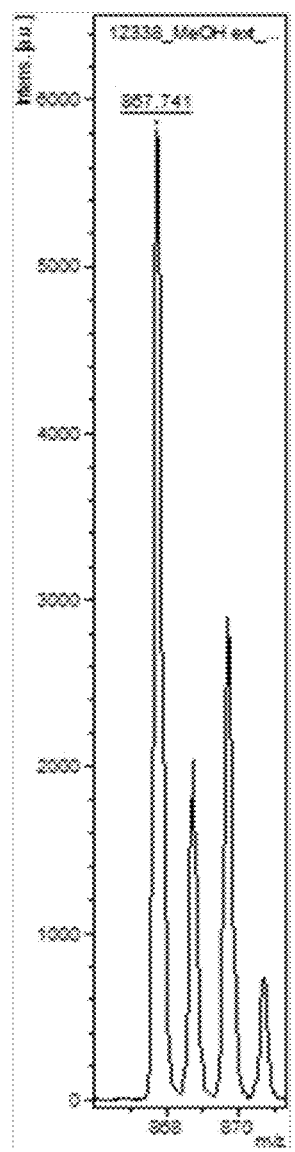
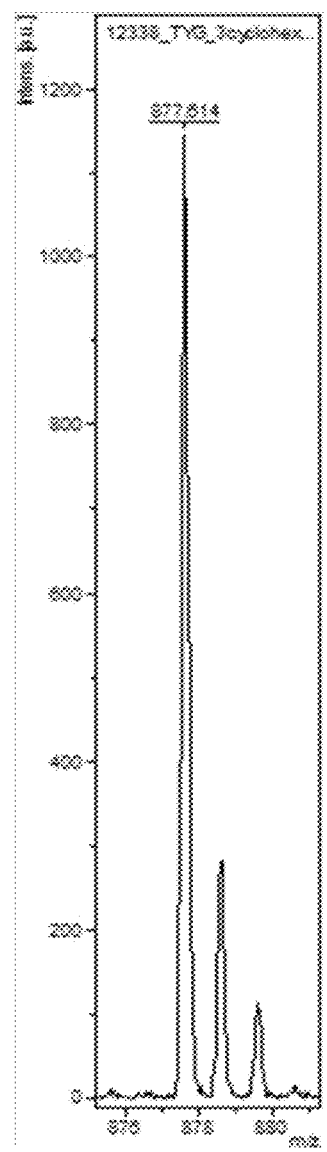
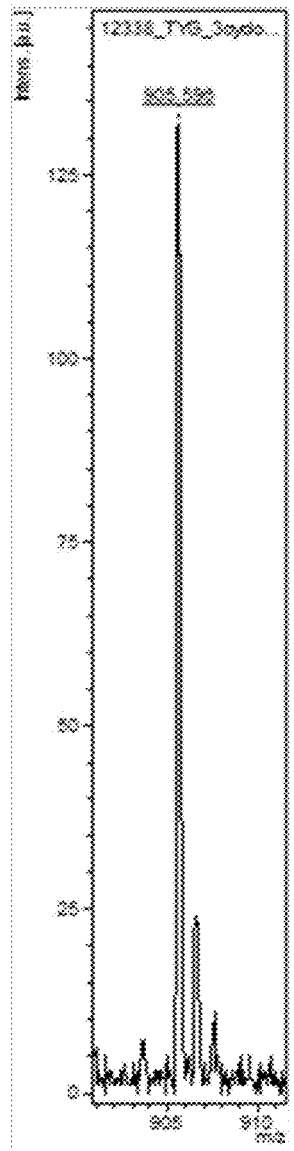
| m/z 867 | m/z 877 | m/z 905 |
| Tun16:1 | 3C6eneCA | 3C6eneCA |
| Ratio  1.0 | 1.29 | 0.12 | m/z 891
1C5eneCA 0.17 m/z 863
3C5eneCA 0.48 m/z 891
3C5eneCA 0.10

OMEGA-ALICYCLIC TUNICAMYCINS AND ANALOGS

FIELD OF THE INVENTION

The invention relates to new tunicamycin structures referred to as omega-alicyclic tunicamycins (OATs), and chemically modified OATs.

BACKGROUND OF THE INVENTION

The development of new and improved antibiotics is a key part of combating antimicrobial resistance. The global antibiotics market size was valued at USD 40.7 billion in 2020 and is expected to expand. Antibiotic adjuvants, which increase the effectiveness of current antibiotics, have the potential for reducing antibiotic usage by requiring lower doses to achieve the same therapeutic value. They show significant promise for medical and agricultural applications. When combined with antibiotics they either block the resistance mechanism or enhance the antimicrobial action of the drug. These adjuvants are able to: 1) reduce the amounts of antibiotics required to treat infections, 2) lower the cost of treatment, an important consideration for veterinary disease when often the approach is to cull, and 3) often increase the potency sufficiently to overcome the mechanisms of resistance.

Tunicamycins (TUN), which are produced by several *Streptomyces* species, are known to dramatically enhance the activity of all β-lactam antibiotics, making them highly desirable as an antibiotic adjuvant. TUN works by inhibiting essential phospho-translocase enzymes (in the TagO and MraY enzyme families) that catalyze the early biosynthesis of bacterial cell walls. This inhibition results in the additional sensitivity of the bacterial cells to β-lactams. Hence, combining TUN with β-lactam antibiotics results in a dramatic synergy that enhances the whole family of penicillin antibiotics.

The assembly of cell walls in bacteria and glycoprotein N-glycosylation in eukaryotes are highly conserved biological processes, the depletion or blocking of which leads to disease states or cell death. The early steps in their biosynthesis use the Leloir-type polyprenol-phosphate glycosylation pathway that has remained relatively unchanged in all three domains of life. The initial, membrane-associated, step is catalyzed by the polyprenylphosphate-N-acetylhexosamine-1-phosphate-transferase (PNPT) enzyme family, which is essential and broadly dispersed in archaea, bacteria, and eukaryote. The TUN and related quinovosamycins (QVM) and streptovirudins (STR), are natural products from diverse *Streptomyces* species and are widely used as an experimental tool to inhibit eukaryotic protein N-glycosylation. TUN are potent inhibitors of the entire PNPT family, resulting in lethal hypo-glycosylation in eukaryotes and the mis-assembly of bacterial cell walls. Hence, any potential for natural TUN as novel antibacterial agents is precluded by the inherent mammalian toxicity.

Thus, development of new TUN antibiotic adjuvants is urgently needed.

SUMMARY OF THE INVENTION

Provided herein are new tunicamycin structures referred to as omega-alicyclic tunicamycins (OATs), and chemically modified OATs.

In an embodiment, the invention relates to an N-acyl-tunicamycin variant comprising small carboxylic acids integrated at the tunicamycin omega-X position, or a chemically-modified variant thereof.

In some embodiments of the invention, the N-acyl-tunicamycin variant has an integrated carboxylic acid derived from ketovaline, ketoleucine, ketoisoleucine, trimethylacetic acid, cyclopropanecarboxylic acid, cyclobutanecarboxylic acid, cyclopentanecarboxylic acid, cyclohexanecarboxylic acid, cycloheptanecarboxylic acid, 3-cyclopentene-1-carboxylic acid, or 3-cyclohexene-1-carboxylic acid.

In some embodiments the invention relates to an N-acyl-tunicamycin variant chemically-modified by quantitative hydrogenation and/or reduction of tunicamycin double bonds.

In an embodiment, the invention relates to an antibacterial composition comprising at least one N-acyl-tunicamycin variant of the invention. In some embodiments of the invention, the antibacterial composition, further comprises an antibiotic, wherein said antibiotic is a β-lactam antibiotic, a non-β-lactam antibiotic, or combination thereof.

In an embodiment, the invention relates to a method of killing Gram-positive bacteria in or on an animal by administering to an animal in need thereof an effective amount of an antibacterial composition comprising at least one N-acyl-tunicamycin variant of the invention. In some embodiments of the invention, the method of killing Gram-positive bacteria in or on an animal comprises administering to an animal in need thereof an effective amount of an antibacterial composition comprising at least one N-acyl-tunicamycin variant of the invention and a β-lactam antibiotic, a non-β-lactam antibiotic, or combination thereof.

BRIEF DESCRIPTION OF THE DRAWINGS

FIG. 5A shows tunicamycin-omega-X, TunR1-omega-X, and TunR2-omega-X. FIG. 5B shows the branched chain acyl groups that may be inserted at the "X" position of omega-tunicamycins. FIG. 5C alicyclic acyl groups that may inserted at the "X" position of omega-tunicamycins.

FIG. 6A shows a schematic of the bacterial PNPT-catalyzed enzyme reaction of UDP-GlcNAc and undecaprenyl phosphate. FIG. 6B shows a schematic structure of tunicamycin, with arrows indicating the double bonds that are hydrogenated in the modified tunicamycins, TunR1 and TunR2. FIG.

6C shows a schematic of the binding interaction mediated by π-π stacking between the uridyl group of tunicamycin and Phe249 in the PNPT uridyl binding pocket. The Phe249 numbering is based on the human PNPT, called hGPT.

Figure 7A:
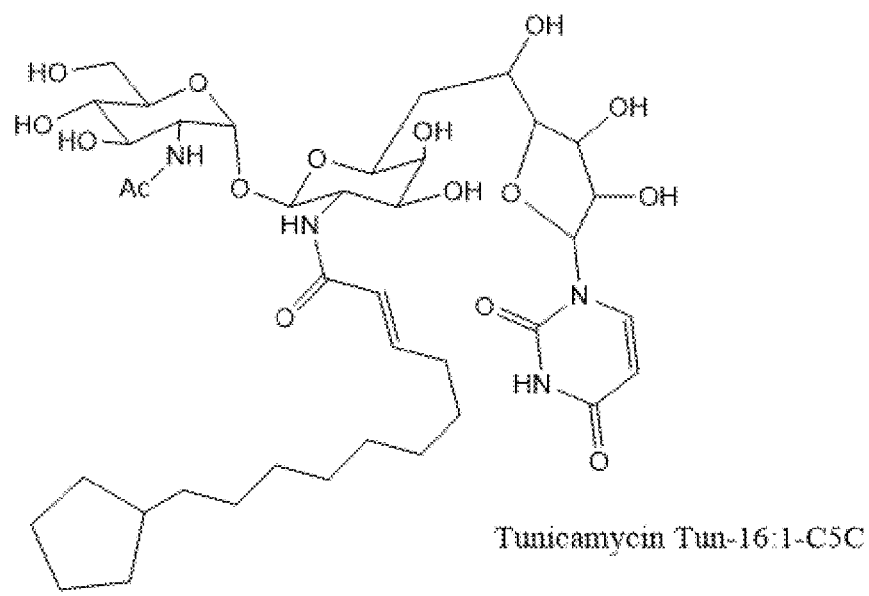
Figure 7A:
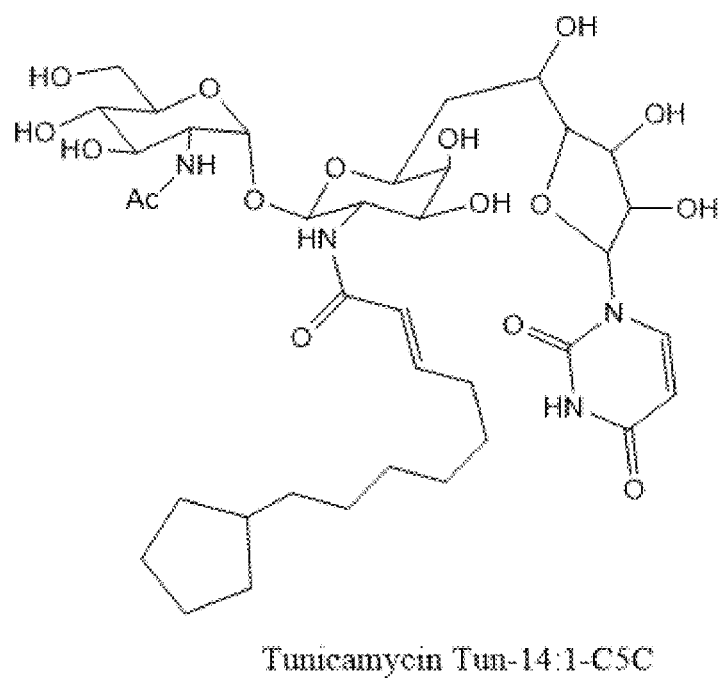
Figure 7B:
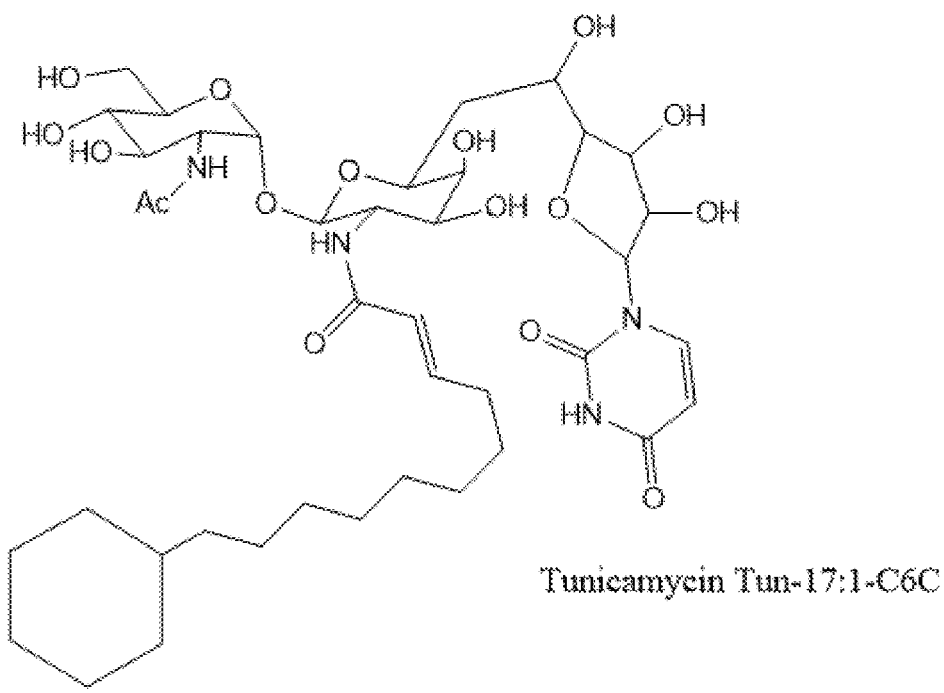
Figure 7B:
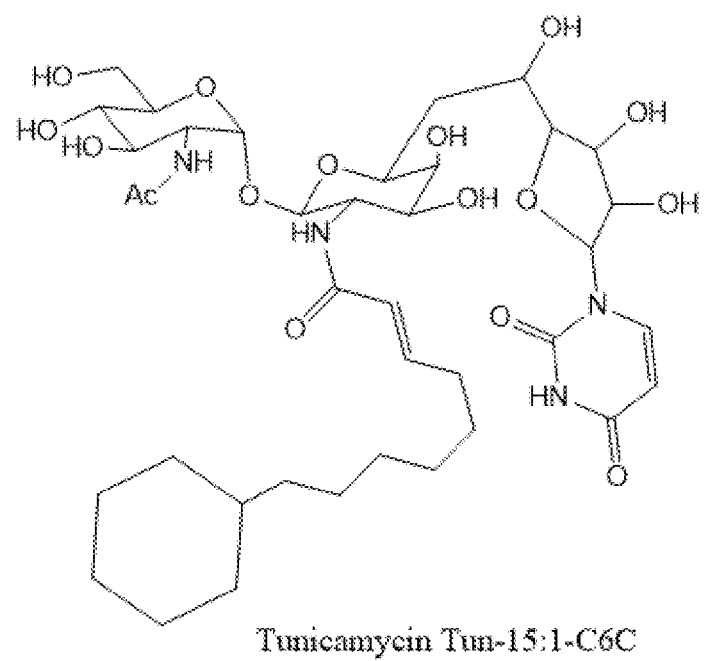
Figure 7C:
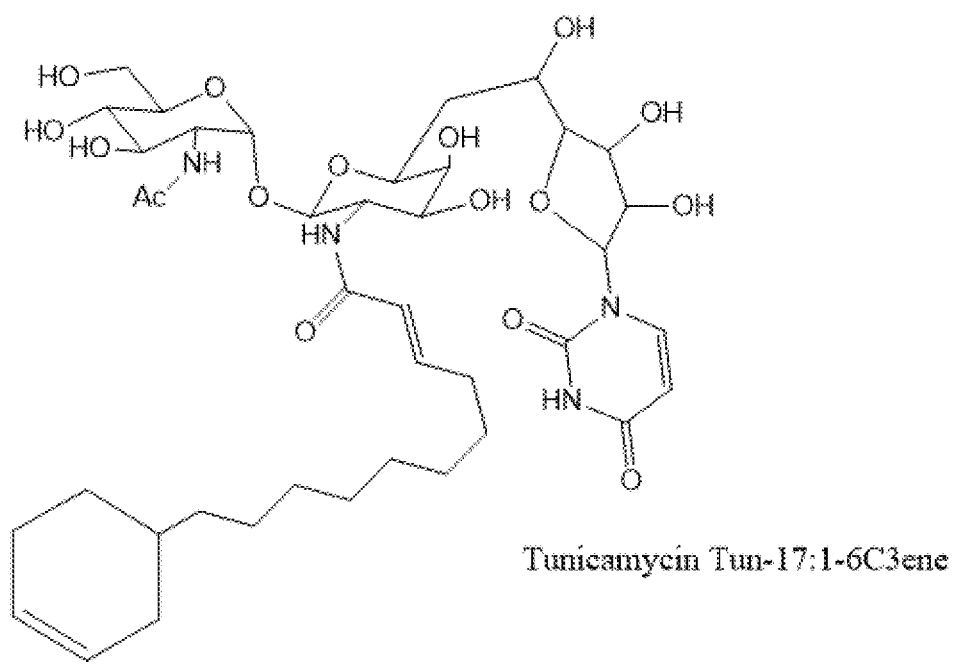
Figure 7C:
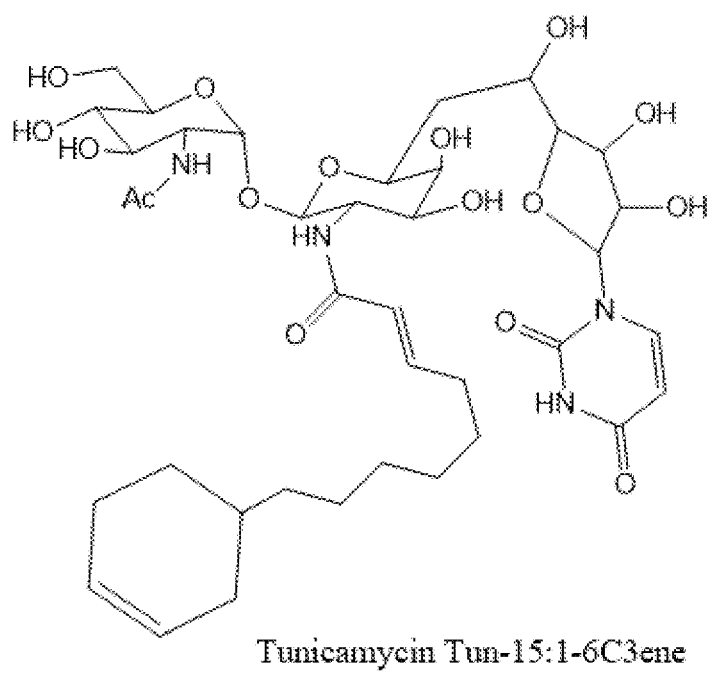

FIG. 7A to FIG. 7C depict examples of omega-tunicamycin structures. FIG. 7A shows examples of C5C-tunicamycins. FIG. 7B shows examples of C6C-tunicamycins. FIG. 7C shows examples of 6C3ene-tunicamycins.

Figure 8A:
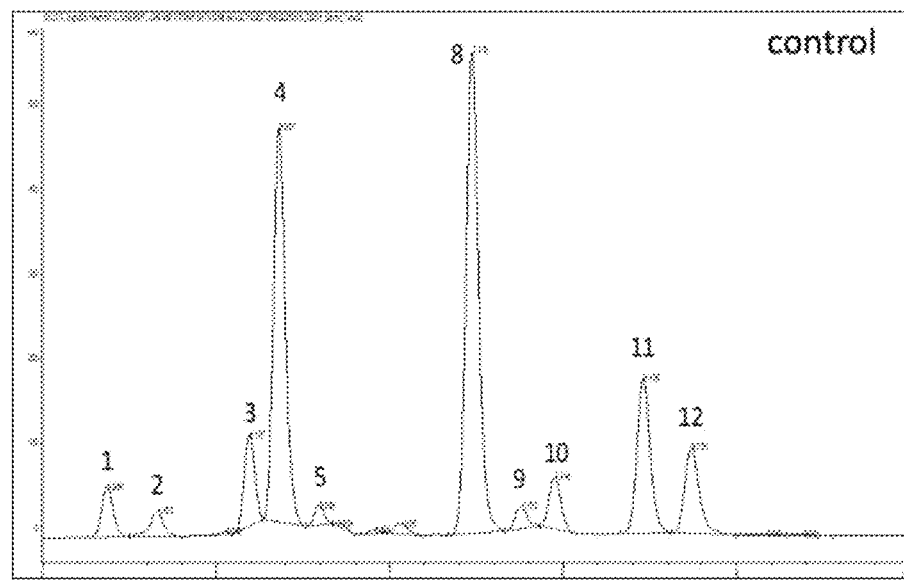
Figure 8B:
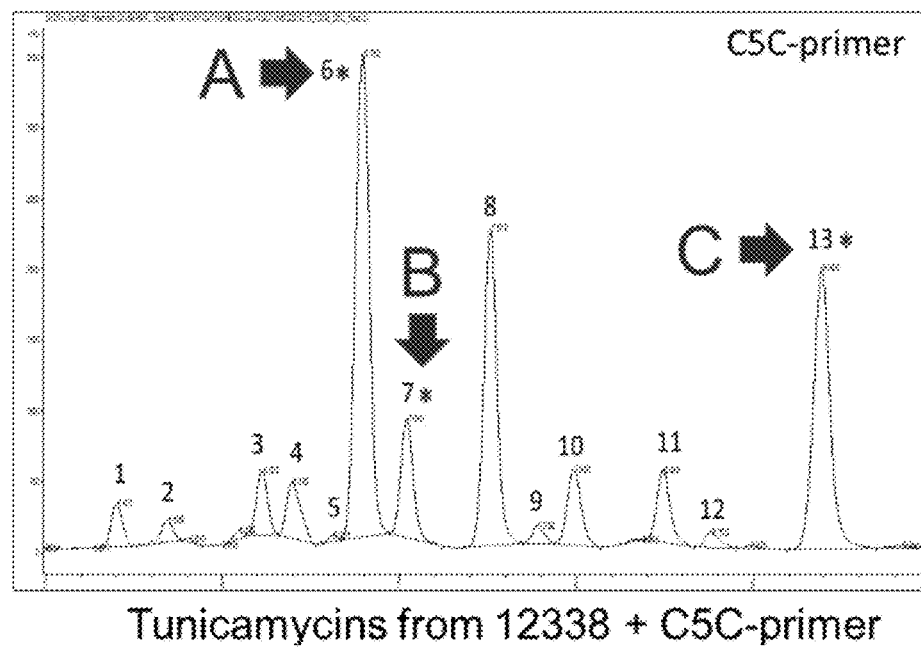
Figure 8C:
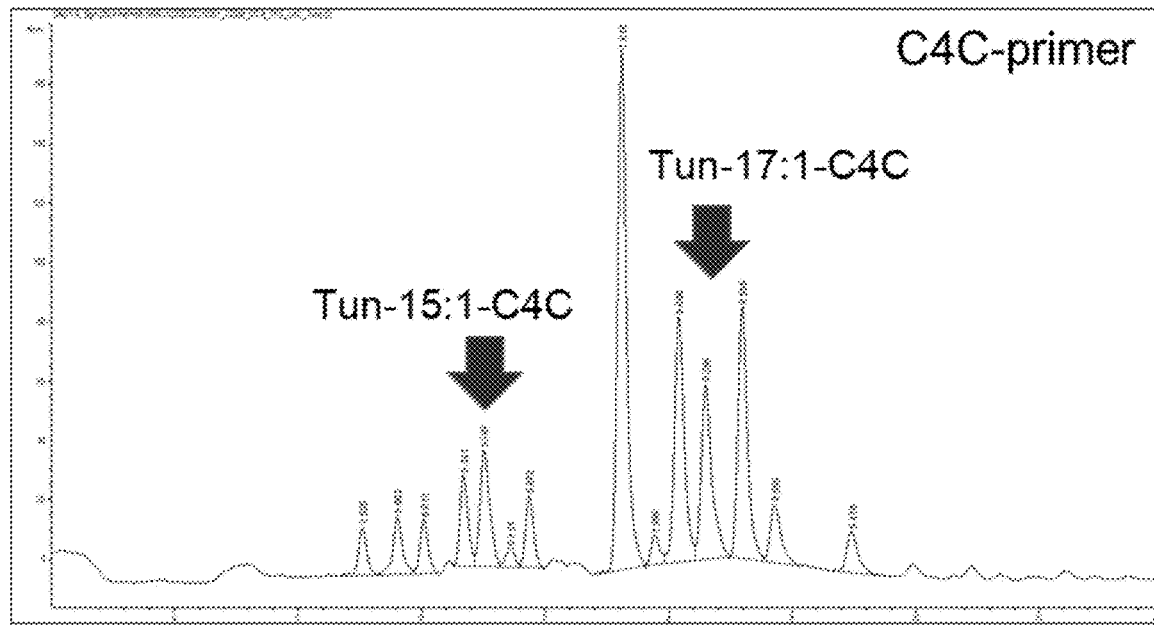
Figure 8D:
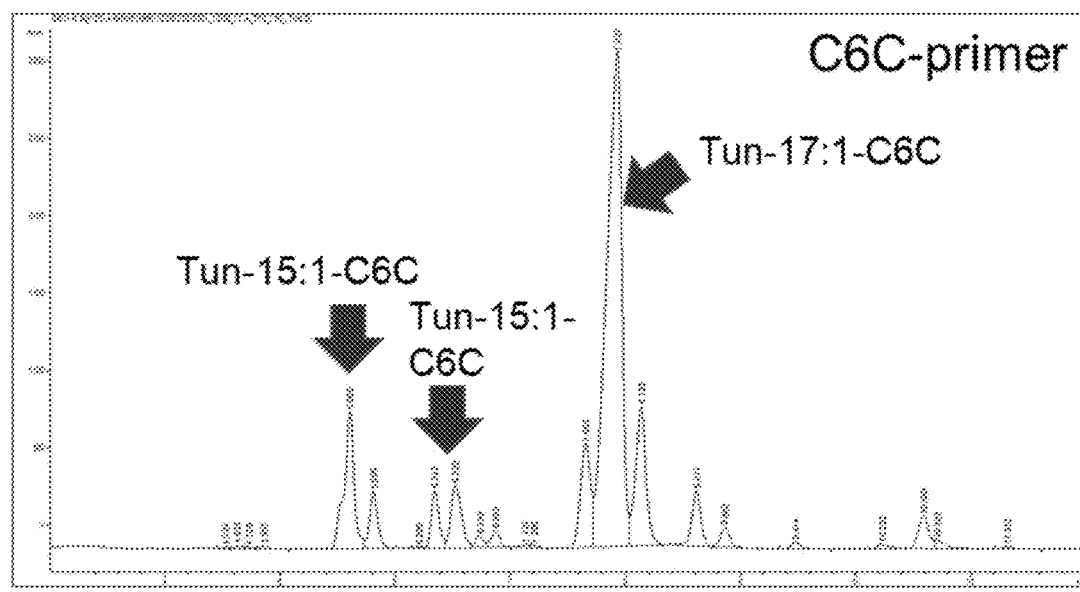
Figure 8E:
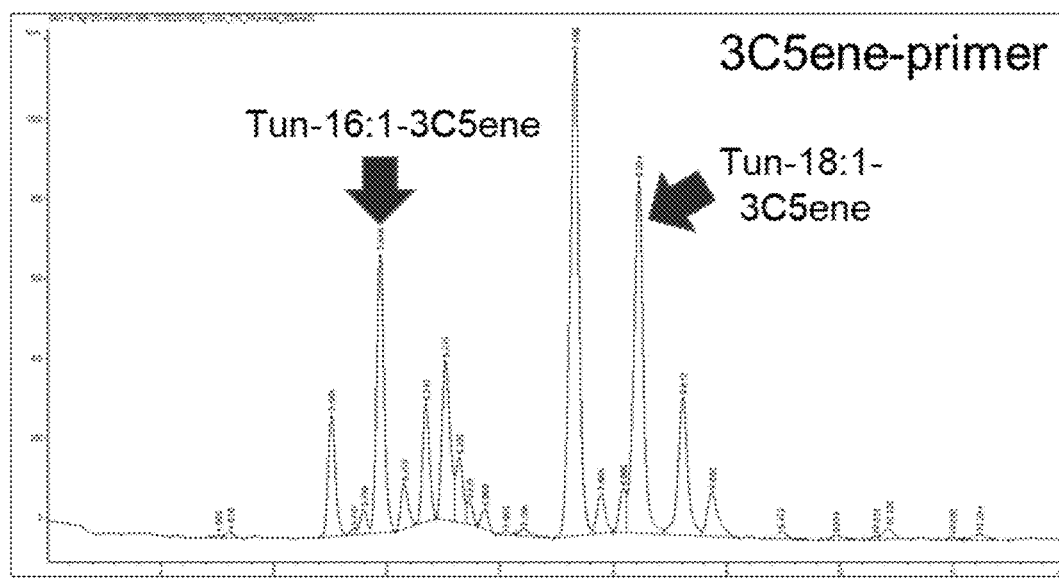
Figure 8F:
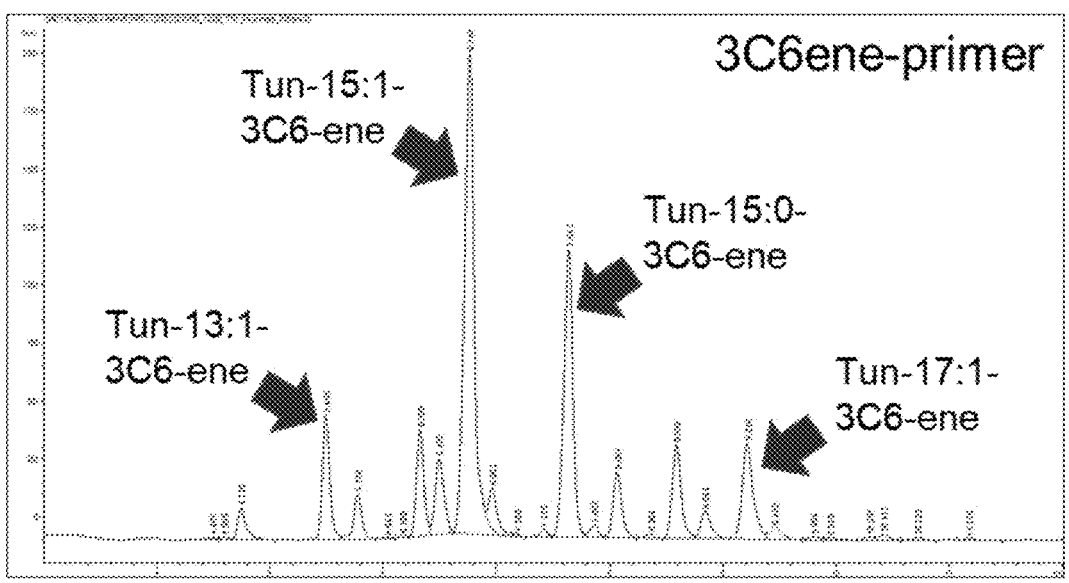

FIG. 8A to FIG. 8F depict reversed-phase HPLC chromatographs for a control tunicamycin and for omega-tunicamycins. FIG. 8A shows a trace for the native tunicamycins obtained from Streptomyces chartreusis NRRL 12338 control. FIG. 8B shows a trace of tunicamycins obtained from 12338+C5C-primer. FIG. 8C shows a trace of tunicamycins obtained from 12338+C4C-primer. FIG. 8D shows a trace of tunicamycins obtained from 12338+C6C-primer. FIG. 8E shows a trace of tunicamycins obtained from 12338+3C5ene-primer. FIG. 8F shows a trace of tunicamycins obtained from 12338+3C6ene-primer. New peaks appearing due to the formation of omega-tunicamycins are indicated by arrows.

Figure 9J:
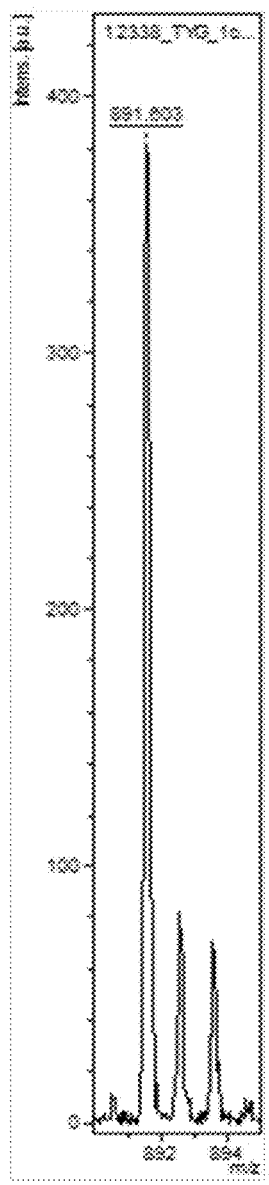
Figure 9K:
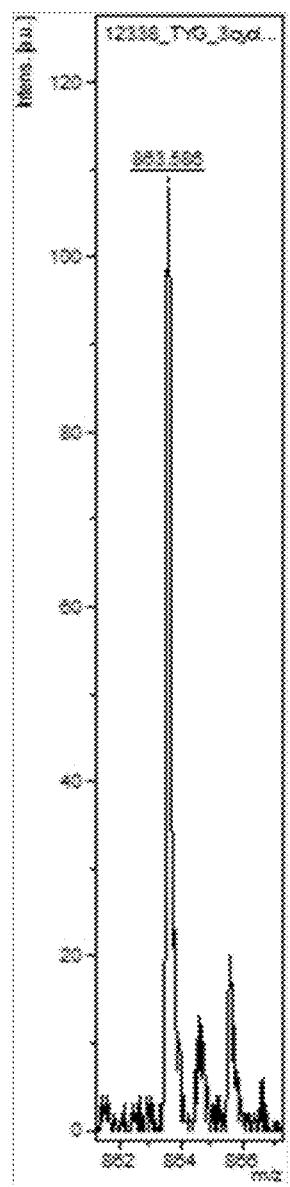
Figure 9L:
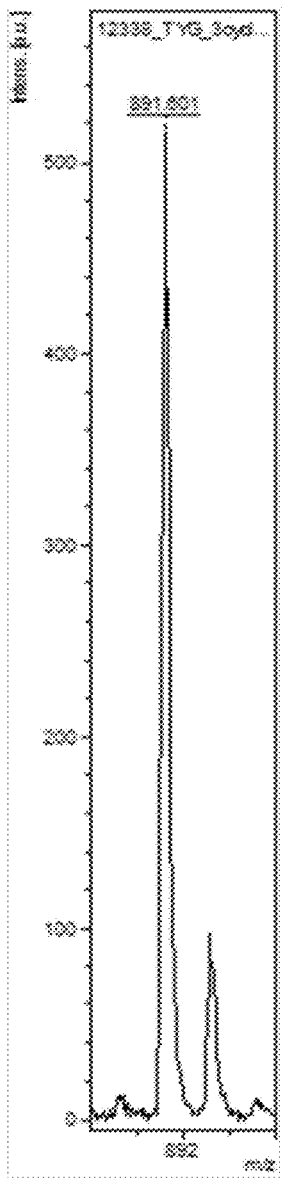

FIG. 9A to FIG. 9L depict graphs of the matrix-assisted laser desorption/ionization mass spectrometry (MALDI-MS) of control and new omega-tunicamycins. FIG. 9A shows MALDI-MS trace at m/z 867 for Tun16:1 (control). FIG. 9B shows MALDI-MS trace at m/z 879 for Tun17:1-C4C. FIG. 9C shows MALDI-MS trace at m/z 865 for Tun16:1-C5C. FIG. 9D shows MALDI-MS trace at m/z 893 for Tun18:1-C5C. FIG. 9E shows MALDI-MS trace at m/z 879 for Tun17:1-C6C. FIG. 9F shows MALDI-MS trace at m/z 893 for Tun18:1-C7C. FIG. 9G shows MALDI-MS trace at m/z 867 for Tun16:1 control. FIG. 9H shows MALDI-MS trace at m/z 877 for Tun16:1-3C6eneCA. FIG. 9I shows MALDI-MS trace at m/z 905 for Tun16:1-3C6eneCA. FIG. 9J shows MALDI-MS trace at m/z 891 for Tun16:1-1C5eneCA. FIG. 9K shows MALDI-MS trace at m/z 863 for Tun16:1-3C5eneCA. FIG. 9L shows MALDI-MS trace at m/z 891 for Tun16:1-3C5eneCA. The quantitative yields produced in the fermentations relative to Tun16:1 are indicated below the traces. The Y axis shows the intensity in arbitrary units (a.u.).

Figure 10A:
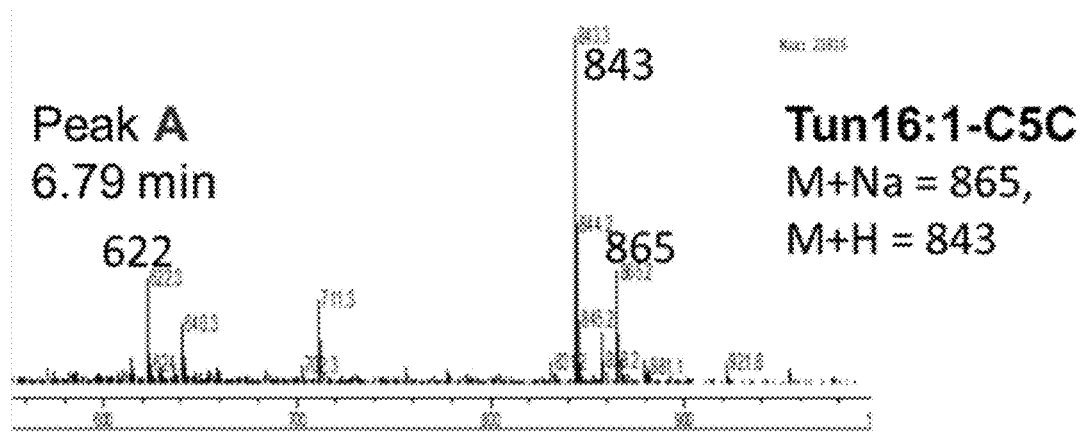
Figure 10B:
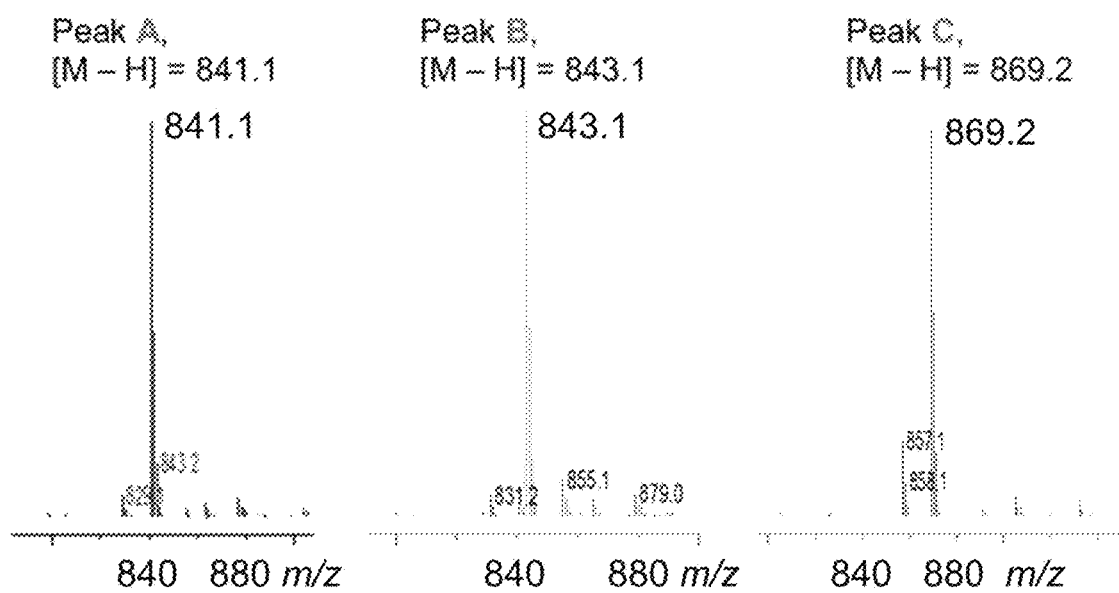

FIG. 10A and FIG. 10B depict graphs of the LC/ESI/MS with positive ion detection for characterization of example OATs. FIG. 10A shows graphs for three different peaks where peak A is at 6.79 minutes and corresponds to Tun16: 1-C5C; peak B is at 7.04 minutes and corresponds to Tun16:0-C5C; and peak and C is at 9.38 minutes and corresponds to Tun18:1-C5C. FIG. 10B shows graphs of the corresponding to the MS negative ions, for example, OATs Tun16:1-C5C, Tun16:0-C5C, and Tun18:1-C5C.

Figure 11:
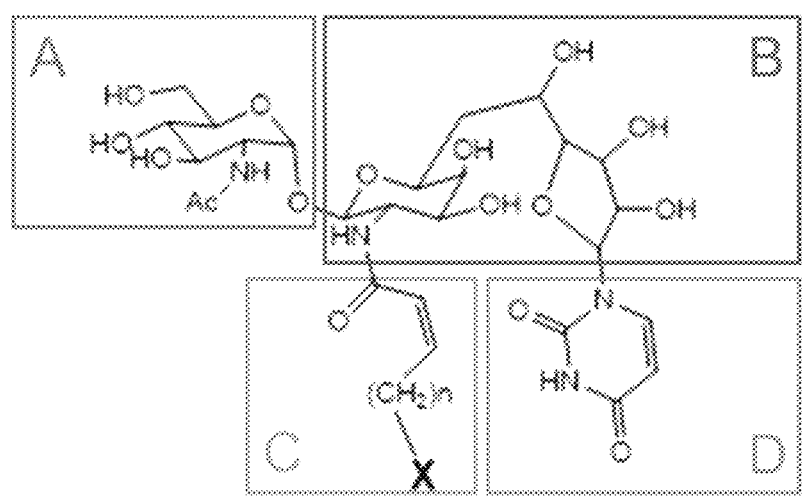

FIG. 11 depicts the four NMR spin systems of the tunicamycin omega-X family. Box A has N-acetylglucosaminyl carbons A1 through A8; Box B has tunicaminyl carbons B1 to B11; Box C has N-acyl chain carbons C1 to Cx; and D has uridyl carbons D1 to D4.

Figure 12A:
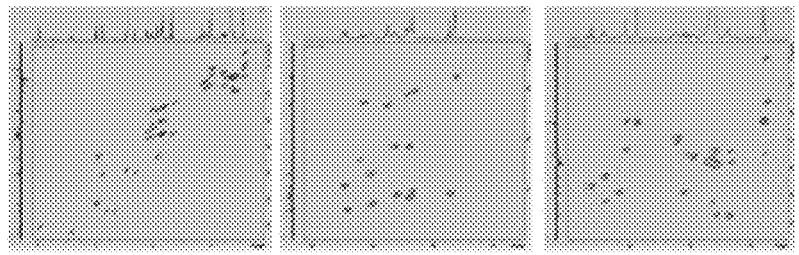
Figure 12B:
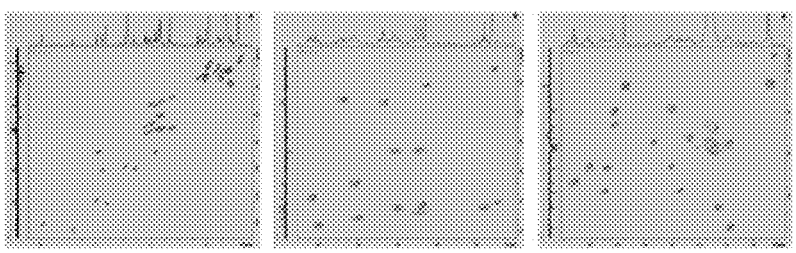
Figure 12C:
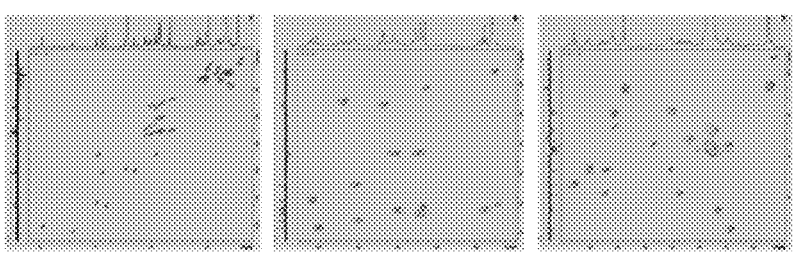
Figure 12D:
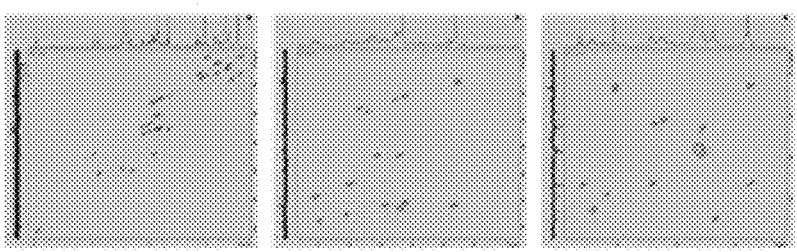
Figure 12E:
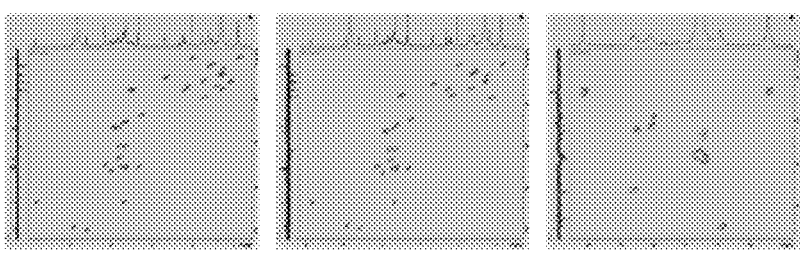

FIG. 12A to FIG. 12E depict NMR HSQC spectra of omega-tunicamycins. FIG. 12A shows the NMR HSQC spectra for 3-C5-ene OAT, with the left panel presenting data for 0 to 8 ppm, center panel presenting data for 2.8 to 4.5 ppm, and the right panel presenting data for 0 to 2.5 ppm. FIG. 12B shows the NMR HSQC spectra for 3-C6-ene OAT, where the left panel presents data for 0 to 8 ppm, center panel presents data for 2.8 to 4.5 ppm, and the right panel presents data for 0 to 2.5 ppm. FIG. 12C shows the NMR HSQC spectra for C5C-TunR1 OAT, where the left panel presents data for 0 to 8 ppm, center panel presents data for 2.8 to 4.5 ppm, and the right panel presents data for 0 to 2.5 ppm. FIG. 12D shows the NMR HSQC spectra for C6C-TunR1 OAT, where the left panel presents data for 0 to 8 ppm, center panel presents data for 2.8 to 4.5 ppm, and the right panel presents data for 0 to 2.5 ppm. FIG. 12E on the left panel shows data for C5C-TunR2 OAT 0.8 to 6.0 ppm; on the center panel shows data for C6C-TunR2 OAT, 0.7 to 6.0 ppm; and on the left panel shows data for C6C-TunR2 0.4 to 2.2 ppm.

Figure 13:
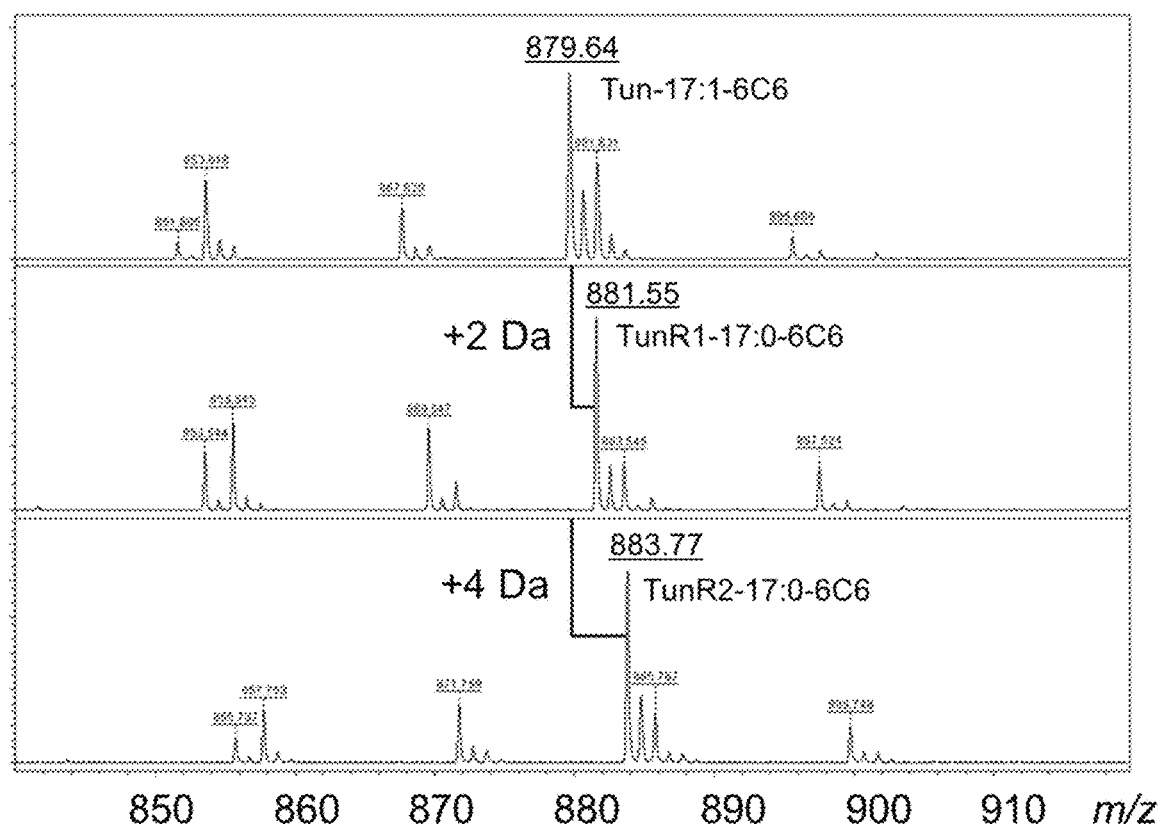

FIG. 13 depicts MALDI-TOF mass spectrometric evidence of the quantitative hydrogenation of Tun-C6C-type omega alicyclic tunicamycins into the corresponding TunR1 and TunR2 OATs analogs. Mass increases 879→881 (2 Da) and 879→883 (4 Da) indicate the reduction of one and two double bonds, respectively.

Figure 14:
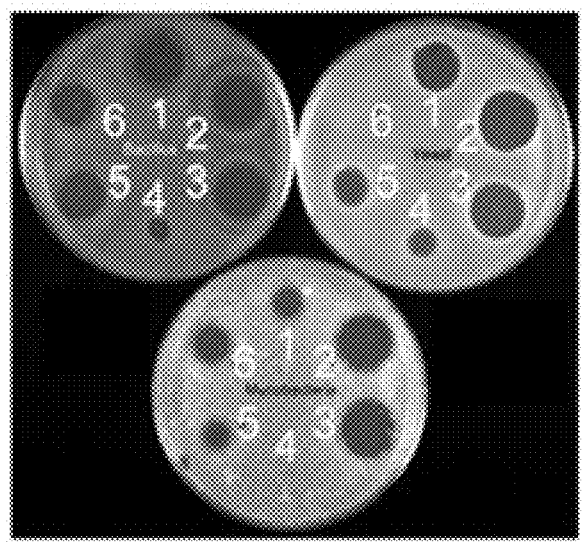

FIG. 14 shows images of the effects of different tunicamycins on Bacillus subtilis (Bacillus) or Saccharomyces cerevisiae (Yeast) growth. Plates on the top were incubated 24 hours at 28° C.; plates on the bottom were incubated 4 hours at 28° C. 1=commercial tunicamycin; 2=TYG control; 3=TYG+C6C; 4=C6C Fr 81 5=C6C TunR21 6=C6C TunR1. Note that compound 5 is selectively active on the Bacillus.

Figure 15A:
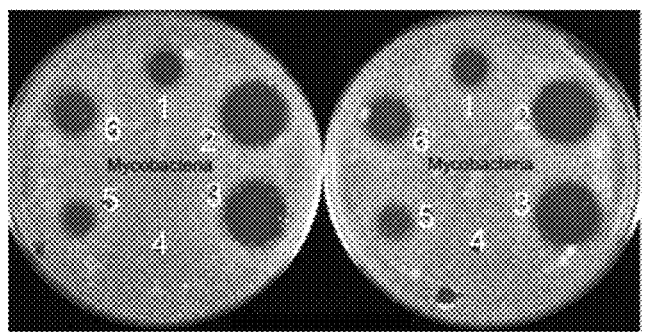
Figure 15B:
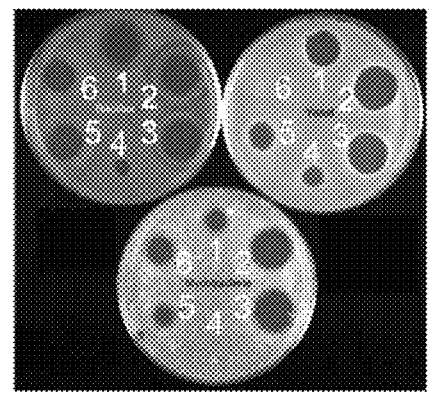
Figure 15C:
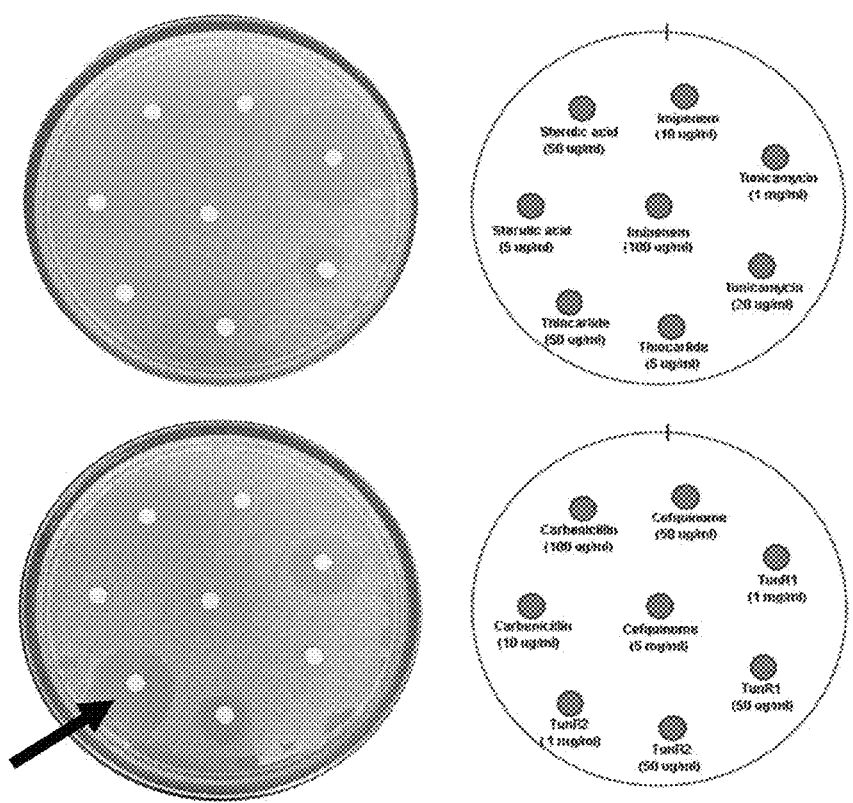

FIG. 15A to FIG. 15C show images of the effects of different tunicamycins on Mycobacterium or yeast growth. FIG. 15A shows the effects on Mycobacterium smegmatis (Mycobacteria). FIG. 15B shows the effect on Bacillus subtilis (Bacillus), Saccharomyces cerevisiae (Yeast) Bacillus subtilis (Bacillus), Saccharomyces cerevisiae (Yeast), and Mycobacterium smegmatis (Mycobacteria). 1=commercial tunicamycin; 2=TYG control; 3=TYG+C6C; 4=C6C Fr 81 5=C6C TunR21 6=C6C TunR1. FIG. 15C shows the effect on Mycobacterium avium subsp. Paratuberculosis. Top plate: center: 100 µg/mL Imipenem Imipenem is a carbapenem antibiotic; in a clock-wise orientation starting from the top: 10 µg/mL Imipenem; 1 µg/mL tunicamycin; 20 µg/mL tunicamycin; 5 µg/mL Thiocarlide; 50 µg/mL Thiocarlide; 5 µg/mL sterulic acid; 50 µg/mL sterulic acid. Bottom plate: center 5 mg/mL Cefquinome; in a clock-wise orientation starting from the top: 50 µg/mL Cefquinome; 1 mg/mL TunR1; 50 µg/mL TunR1; 50 µg/mL TunR2; 1 mg/mL TunR2; 10 µg/mL Carbenicillin; 100 µg/mL Carbenicillin.

Figure 16:
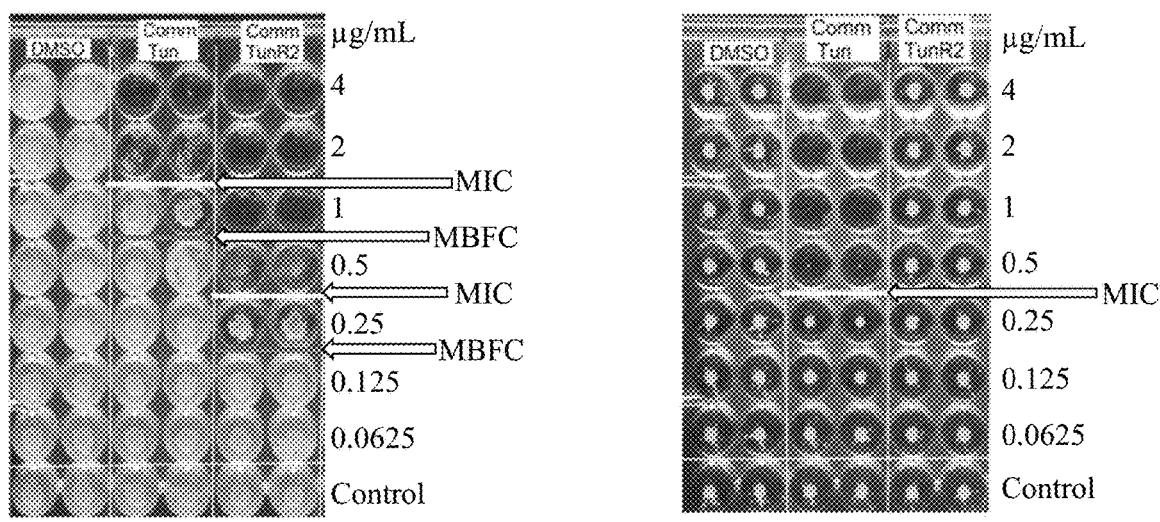

FIG. 16 shows the effect on Mycobacterium smegmatis and yeast growth and biofilm formation of different concentrations of tunicamycin and TunR2. Left panel shows results for Mycobacterium smegmatis grown in TYG for 6 days at 37° C., and right panel shows results for yeast grown in TYG for 24 hours at 37° C. In each plate, left two columns are treated with DMSO, center two columns are treated with tunicamycin; right two panels are treated with TunR2. The concentration in µg/mL is indicated on the right. Arrows show the concentration at which there is mycobacterial growth inhibition (MIC), or biofilm formation is blocked (MBFC).

Figure 17:
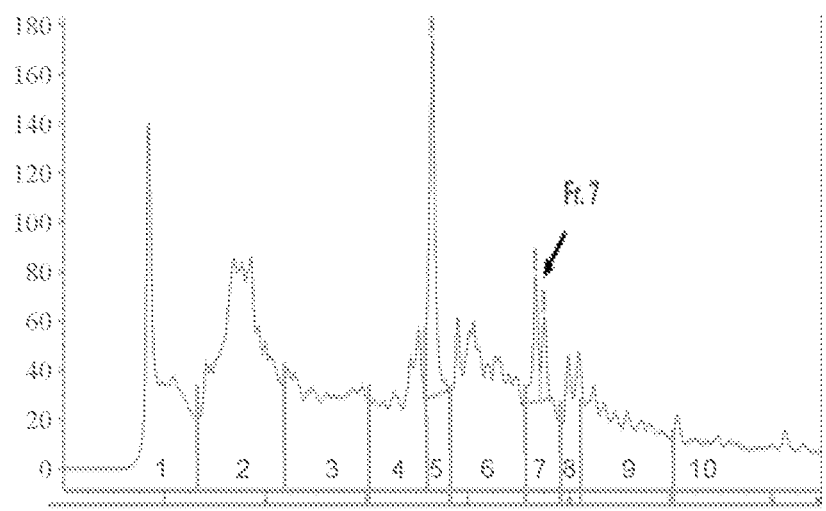
Figure 17:
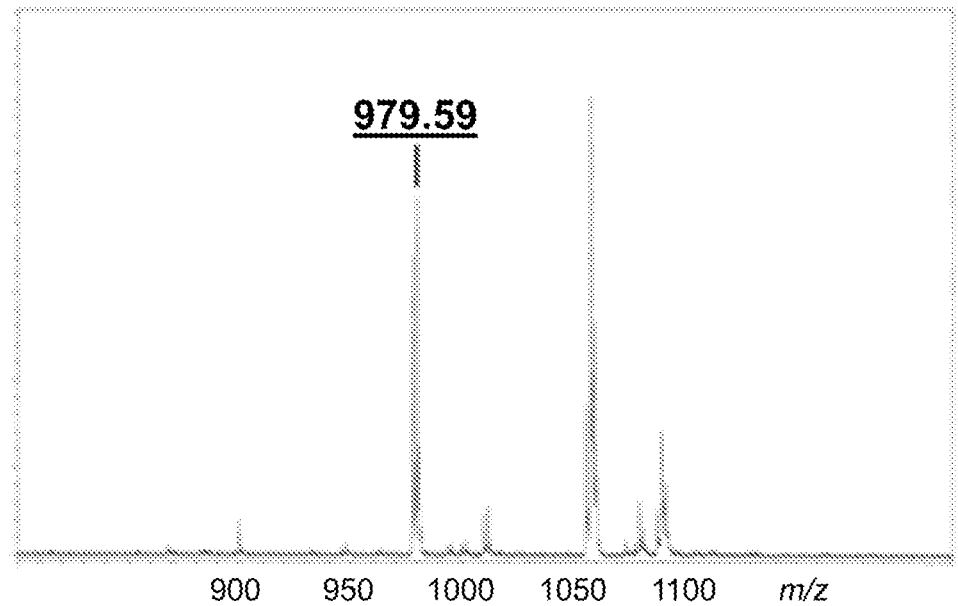

FIG. 17A and FIG. 17B depict graphs of the reverse phase HPLC trace and MALDI-TOF/MS analysis of brominated Tun-C6C-3-ene. FIG. 17A shows the reverse phase HPLC trace. Fraction 7 is indicated by an arrow (Fr. 7). FIG. 17B shows the MALDI-TOF/MS analysis at m/z 979.59 of fraction 7.

DETAILED DESCRIPTION

The present invention relates to new tunicamycin structures comprising metabolically integrated into the terminus of the TUN N-acyl groups via the Streptomyces branched chain fatty acid pathways.

The invention relates to novel tunicamycin structures resulting from the integration of small, alkylcyclic organic acids into the terminus of the TUN N-acyl chains via the *Streptomyces* branched chain fatty acid pathways. The inventors refer to the new tunicamycin structures produced as omega-alicyclic tunicamycins (OATs).

Figure 1:
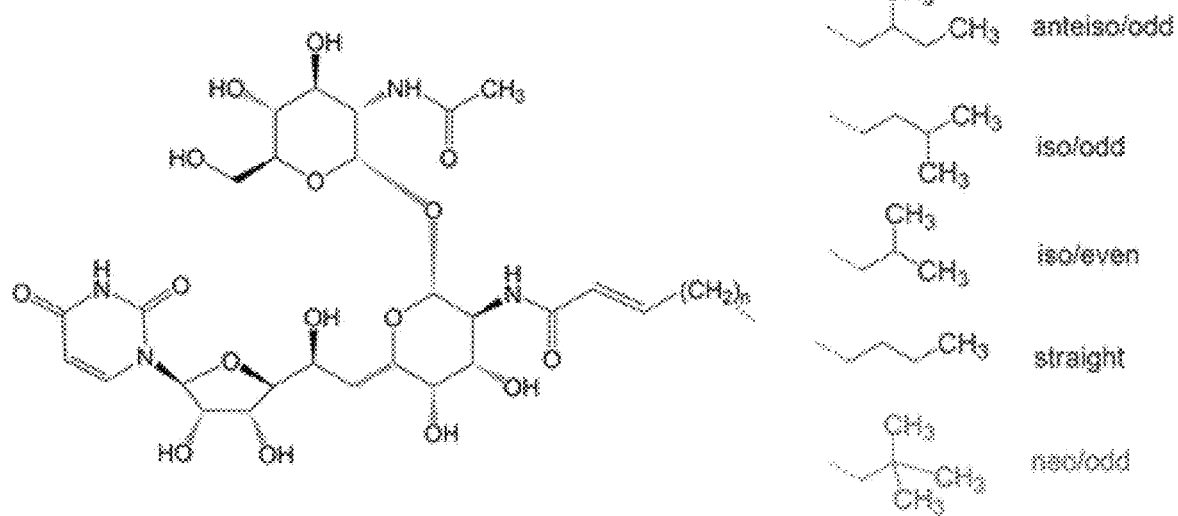
FIG. 1 depicts structures of tunicamycin branched variants as described in N P J Price et al. (2021, "Branched Chain Lipid Metabolism As a Determinant of the N-Acyl Variation of *Streptomyces* Natural Products," ACS Chem. Biol. 16:116-124.

The tunicamycins (TUN) are bioactive materials that vary in the structure of the N-acyl group attached to them, as shown in FIG. 1. These N-acyl groups at least partly determine antibacterial properties and the associated eucaryotic toxicity of the naturally occurring TUN. The TUN N-acyl chains differ in chain length (typically 13-18 carbons long), the presence of double bonds, and in the type of branching found at the terminus of the acyl chains. Prior X-ray crystallographic and biochemical studies by the inventors have shown that each of these structural features have a profound effect on the bioactivity and toxicity. The inventors have also shown that the TUN N-acyl branching pattern is largely specified by the availability of branched chain amino acids (valine, leucine, or isoleucine) during the fermentation of tunicamycin-producing *Streptomyces*. Hence, the amino acids are the biochemical precursor of the TUN N-acyl groups, and are introduced via the *Streptomyces* fatty acid metabolism.

The recently solved PNPT-TUN complex structure has revealed the basis for inhibition of N-glycosylation. The human homolog of the PNPT target protein (hGPT) TUN forms a complex with the TUN N-acyl chain in a groove between three transmembrane domains, TMs 4, 5, and 9a (J Yoo, 2018, "GlcNAc-1-P-transferase-tunicamycin complex structure reveals basis for inhibition of N-glycosylation," Nat. Struct. Mol. Biol. 25(3): 217-224). This has also been proposed as the binding site for the polyprenyl chain of undecaprenyl phosphate (C55-P) in MraY, one of the bacterial forms of PNPT (BC Chung, 2013, "Crystal structure of MraY, an essential membrane enzyme for bacterial cell wall synthesis," Science 341 (6149): 1012-1016). Indeed, the differences between the polyprenol binding sites in human GPT and bacterial MraY partly determines the high selectivity that each enzyme exhibits for its respective substrate, either dolichol-P or C55-P (J Yoo, supra; N P J Price et al., 2017, "Modified tunicamycins with reduced eukaryotic toxicity that enhance the antibacterial activity of lactams," J. Antibiot. 70" 1070-1077).

Figure 2:
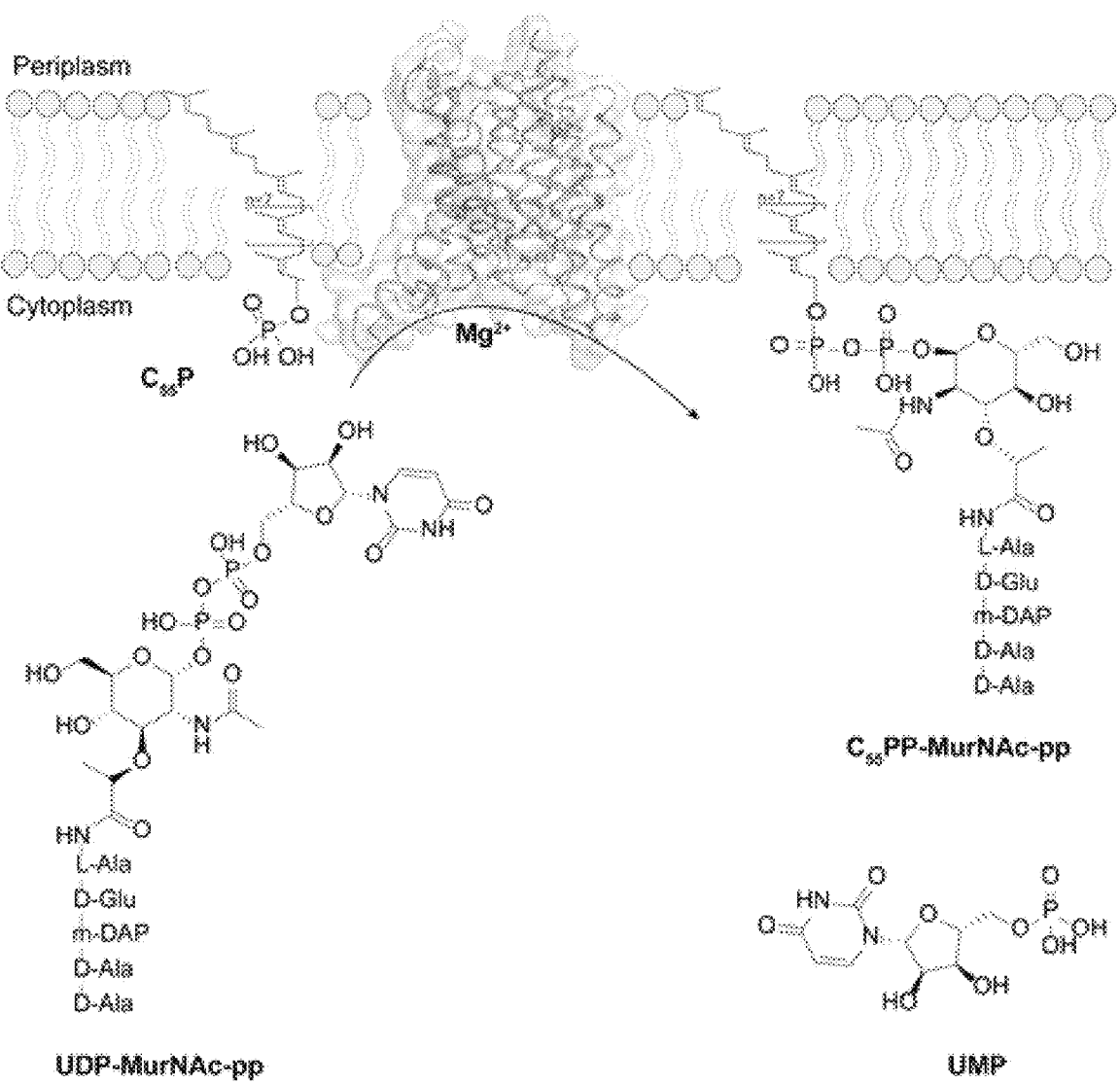
FIG. 2 depicts a schematic diagram of the enzymatic reaction catalyzed by the bacterial membrane-bound protein MraY on the cytoplasmic side of the inner bacterial membrane.

A schematic diagram of the enzymatic reaction catalyzed by bacterial membrane-bound protein MraY on the cytoplasmic side of the inner membrane in bacteria is shown in FIG. 2. The lipid substrate $C_{55}P$ in the membrane reacts with the soluble substrate UDP-MurNAc-pentapeptide (UDP-MurNAc-pp) in a reaction catalyzed by MraY protein, yielding $C_{55}$PP-MurNAc-pentapeptide ($C_{55}$PP-MurNAc-pp) and UMP. The MraY protein is the first step in cell wall assembly in bacteria and is a known target for inhibition by tunicamycins. Hence, TUN blocks the biosynthesis of cell walls in bacteria, with a corresponding potent antibacterial activity.

Figure 3:
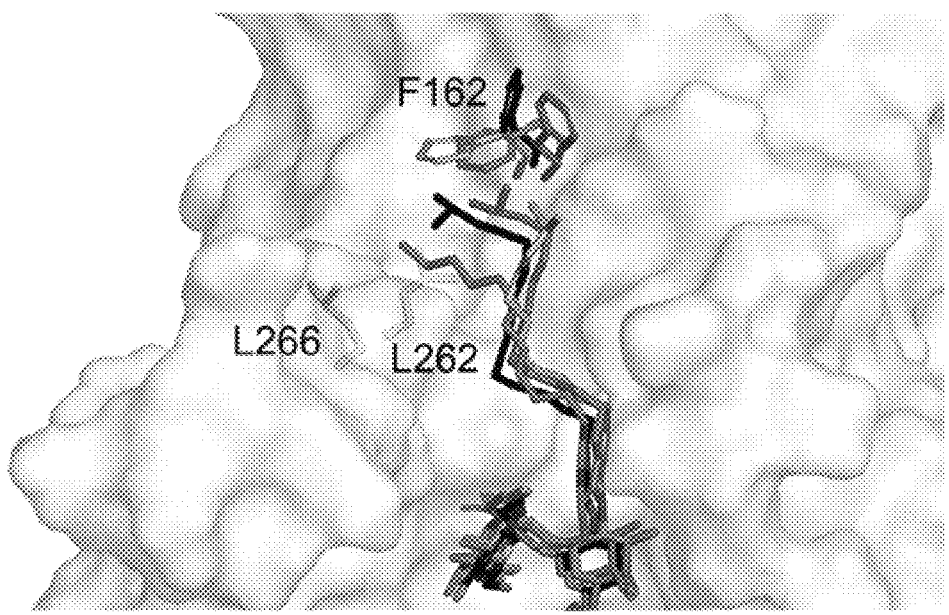
FIG. 3 depicts an X-ray crystallography structure of the tunicamycin target protein, MraY. The location of the phenylalanine F162 residue in the hydrophobic cavity, and the two leucine residues L262 and L266 that interact with Tun 15:1-iso are indicated.

The data indicates the importance of the Tun N-acyl chain length and the branching type at the end of the chain (i.e., the omega position). Tunicamycin N-acyl variants (Tun 14:1-iso, Tun 15:1-iso, Tun 16:1-iso, and Tun 17:1-iso) bind to the hydrophobic cavity of bacterial MraY (J K Hakulinen et al., 2017, "MraY-antibiotic complex reveals details of tunicamycin mode of action," Nat. Chem. Biol. 13 (3): 265-267; J Herring et al., 2018, "Structural basis for selective inhibition of antibacterial target MraY, a membrane-bound enzyme involved in peptidoglycan synthesis," Drug Discov. Today 23:1426-1435). FIG. 3 presents the X-ray crystallography structure of the tunicamycin target protein, MraY. The conformation of the phenylalanine F162 residue in the hydrophobic cavity is shown to bind to the omega-terminal of the various tunicamycin N-acyl chains. The two leucine residues L262 and L266 that interact with Tun 15:1-iso are also displayed. Hence, the omega-termini of tunicamycins are important for efficient binding to the target proteins (PNPT enzyme family) in bacteria and eukaryotes.

The inventors showed previously that TUN variants that lack the trans-2,3-double bond in the N-acyl group are considerably less toxic to eukaryotes but that nevertheless fully retain the antibacterial activity (N P J Price, 2017, supra). Hence, TUN that are catalytically hydrogenated at this position or at the uridyl double bond, hold considerable promise as novel mode-of-action antibacterial adjuvants. The resulting modified tunicamycins (called TunR1 and TunR2) are strongly antibacterial and enhance the antibacterial activity of beta-lactam antibiotics, and with greatly reduced eukaryotic toxicity compared with the natural TUN. Semi-synthetic "Tun-X,X" analogs have also been reported by others in which both the TUN N-acyl and N-acetyl groups are chemically replaced by various short aliphatic acyl chains (Y Y Dong et al., 2018, "Structures of DPAGT1 Explain Glycosylation Disease Mechanisms and Advance TB Antibiotic Design," Cell 175(4):1045-1058). Compound Tun-9,9 was reported as being 5-times more potent than natural tunicamycin against *Mycobacterium tuberculosis* (Mtb), while inhibiting the same target protein. In contrast, the eukaryotic toxicity of the Tun-X,X analogs against cultured mammalian cell lines (HEK293, HepG2, Raji cells; $LD_{50}$=51.2, 44.7, and 26.8 µgmL$^{-1}$, respectively) was low relative to natural tunicamycin ($LD_{50}$=>400 µg·mL$^{-1}$) (Dong 2018, Supra). However, whether these compounds enhance the beta-lactams antibiotics in a similar manner to TunR1, TunR2, or to native tunicamycin has not yet been assessed.

The preceding highlights the importance of the chain length and of the omega-position substituents on the TUN N-acyl groups for both the antibacterial activity and for relative mammalian toxicity. TUN is not a single compound but rather it is comprised of several N-acyl variants with either an N-acetylglucosaminyl (TUN, STV) or an N-acetylquinovosaminyl (QVM) headgroup, which are substituted with various branched chain N-acyl groups. We evaluated the biosynthesis of the various naturally occurring TUN branching-chain types by several different TUN-producing *Streptomyces* species [Price, 2021]. We noted the incorporation of deuterated branched chain amino acids (dVal, dLeu, dIle) into the termini of both TUN N-acyl groups and also into the corresponding cellular membrane lipids of these strains. Hence, Leu and Ile are the precursors of odd chain acyl groups, iso- and anteiso-branch types, respectively, and Val of iso-branched even chains. These finding are also consistent with the known BCFA biosynthetic pathways for other Gram-positive bacteria. We conclude that the branched chain amino acids (Val, Leu, and Ile) are the lipid precursor of fatty acids and tunicamycins via known coenzyme A directed biosynthetic pathways, and that the specific fatty acids used for biosynthesis tunicamycins is directed by the TUN-specific acyl carrier protein gene, TunK (FIG. 4; Price et al, 2020).

Figure 4:
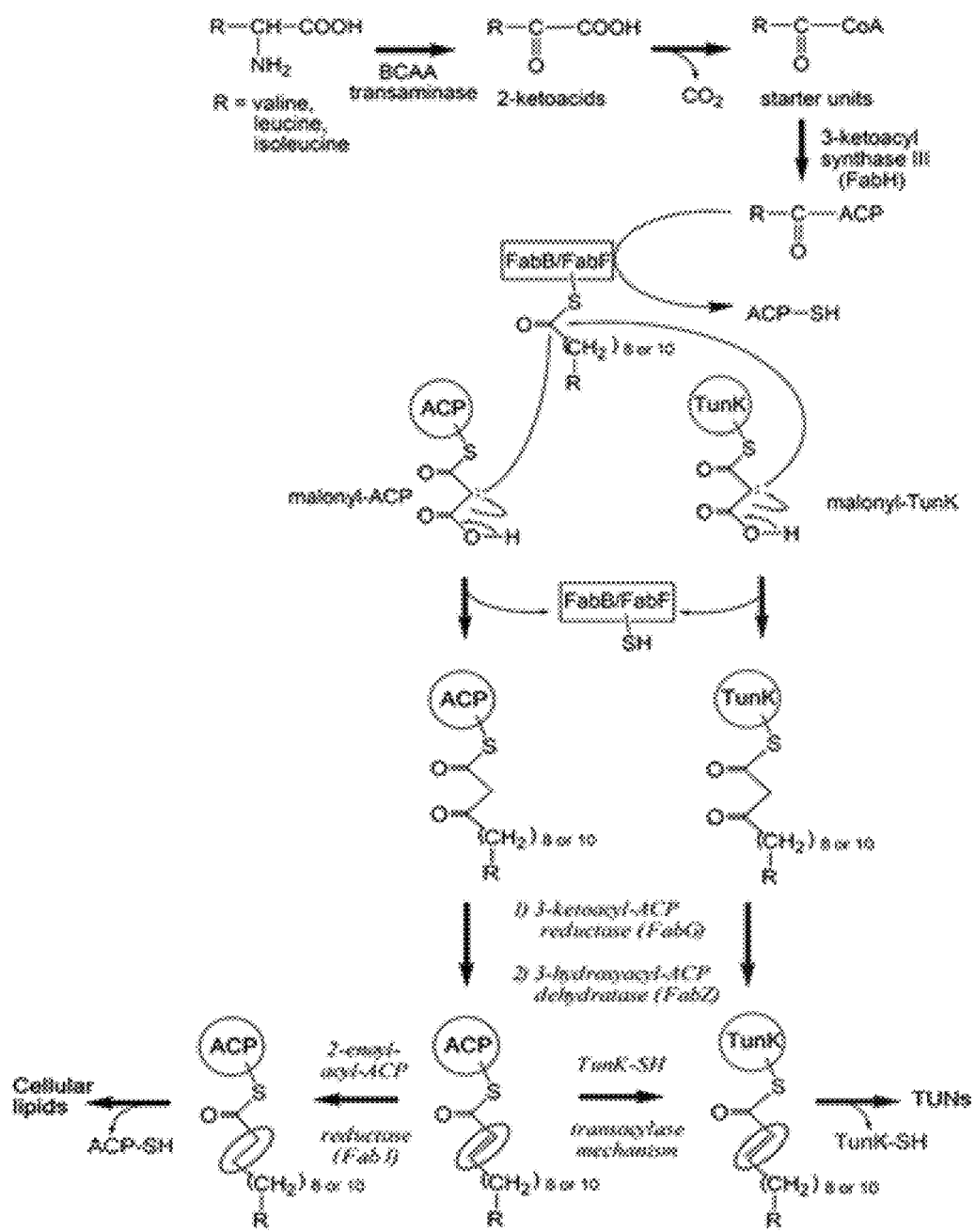
FIG. 4 depicts a schematic diagram of branched-chain fatty acid (FA) intermediates for TUN N-acyl variants and cellular FA on the TUN-specific acyl carrier protein (TunK) and the nonspecific cellular ACP.

As seen in FIG. 4, biosynthesis of branched-chain FA intermediates for TUN N-acyl variants and cellular FA on the TUN-specific acyl carrier protein (TunK) and the non-specific cellular ACP, respectively. The TunK is selective for 2,3-unsaturated BCFA destined for TUN biosynthesis and also for the selective small alicyclic carboxylic acids disclosed in this patent.

Based on these finding we decided to investigate the use of other small carboxylic acids as potential acceptor primers for the biosynthesis of novel and unique N-acyl tunicamycin variants. The inventors initially found that the substrate-specified biosynthesis of tunicamycin N-acyl variants can be achieved by inclusion of a variety small organic acids into the culture media of tunicamycin-producing actinomycetes strains. Small organic acids we found that are able to act as fatty acid precursors are 1) ketovaline, 2) ketoleucine, 3) Ketoisoleucine, 4) trimethylacetic acid (TMA, also called pivulate), and 5) various alicyclic small organic carboxylic acids as described in this patent.

Figure 5A:
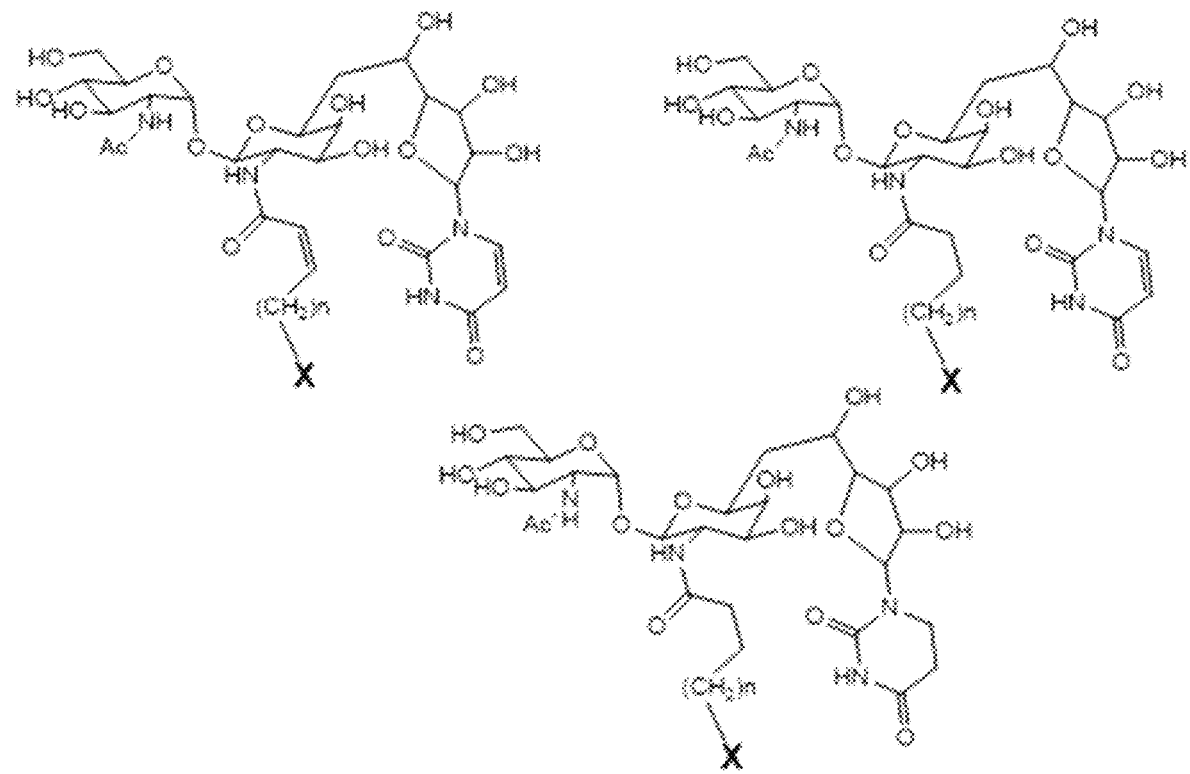
FIG. 5A to FIG. 5C depict omega-alicyclic tunicamycins, branched chain acyl groups, and omega-alicyclic acyl groups used in the preparation of omega-alicyclic tunicamycins.
Figure 5B:
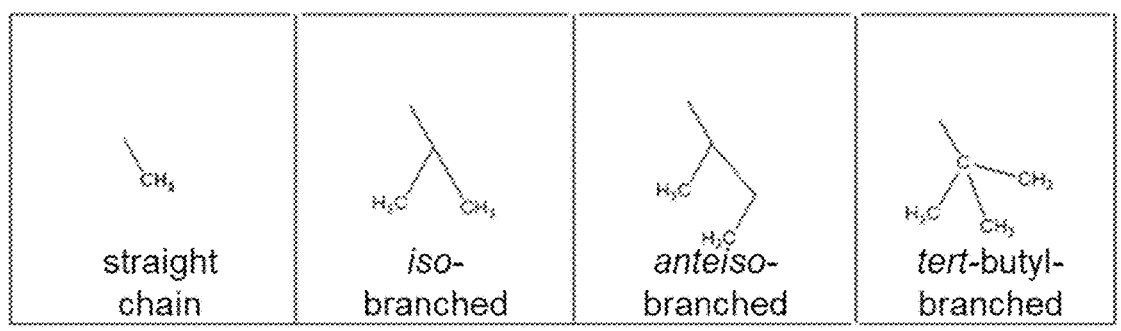
Figure 5C:
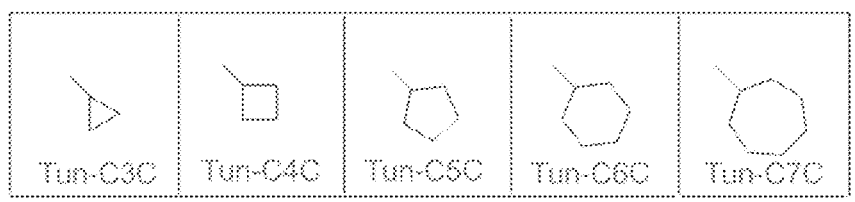
Figure 6A:
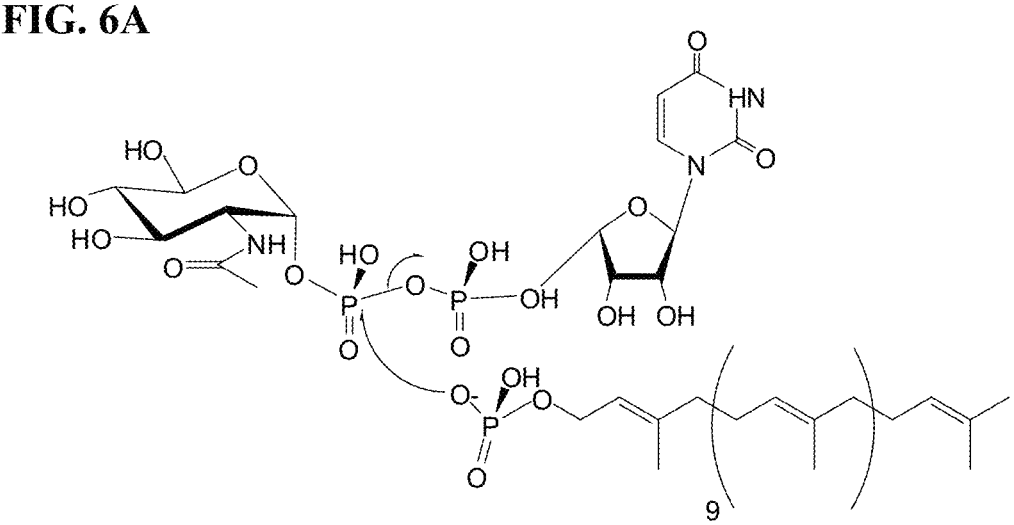
FIG. 6A to FIG. 6C depict schematics of bacterial synthesis of tunicamycin, modified tunicamycins, and tunicamycin binding interaction mediated by π-π stacking.
Figure 6B:
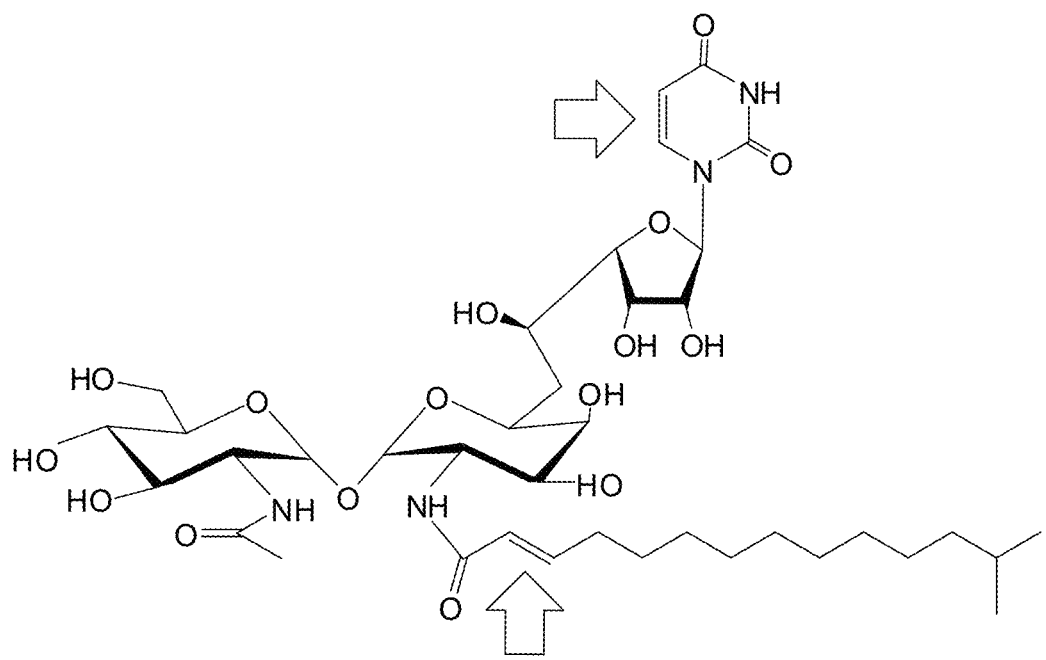
Figure 6C:
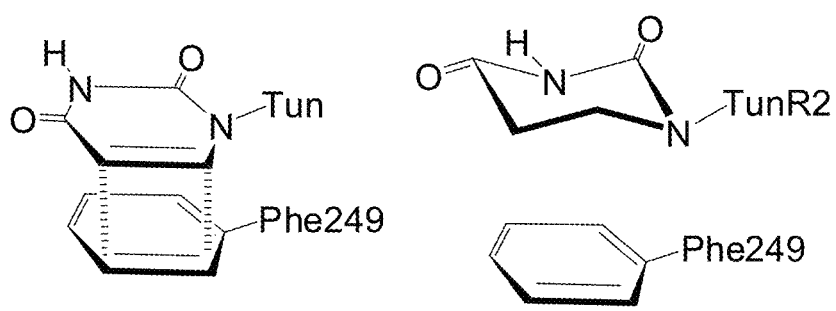

The small alicyclic organic carboxylic acids are incorporated into the terminus of the N-acyl groups of the tunicamycins (the so called "omega" X position, FIG. 5) to generate new omega-alicyclic tunicamycins (OATs), that are previously unknown compounds, and have various and unexpected biological activities. These novel OATs structures are the subject of the current patent. The list of small alicyclic carboxylic acids that we show to be incorporated into OATs are the cycloalkane acids: 1) Cyclopropane-carboxylic acid (C3C); 2) Cyclobutane-carboxylic acid (C4C); 3) Cyclopentane-carboxylic (C5C); 4) Cyclohexane-carboxylic acid (C6C); 5) Cycloheptane-carboxylic acid (C7C) (see FIG. 5), and the corresponding cycloalkene acids: 6) Cyclopent-3-enyl (C5C-3-ene); and 7) Cyclohex-3-enyl (C6C-3-ene). The inventors note that at the time of writing, these alicyclic carboxylic acids are all commercially available and for relatively low cost. The inventors also note that the de novo full chemical synthesis of tunicamycins is challenging and expensive, and this has to date limited the scope of medicinal and agricultural applications for this class of compounds.

The inventors also investigated other small carboxylic acids as potential precursors, but which they found do not incorporate into the tunicamycins, including isopropyl, isobutyl, phenylacetyl, trifluoroacetyl, chloroacetyl, benzoic acid, or the non-branched amino acids. The inventors also investigated several heterocycle rings containing N or O atoms in the ring, none of which worked. The inventors conclude that there is a highly selective biosynthetic pathway in tunicamycin-producing Actinomycetes that is able to activate certain small alicyclic acids (listed above as 1-7) as their ACP-conjugated precursors, which are then elongated by 2-carbon fatty acid chain extension and incorporated into novel OATs tunicamycins by way of the TunK acyl carrier protein as shown in FIG. 4.

FIG. 5A shows omega-alicyclic tunicamycins (OATs; Tunicamycin-omega-X) with various X groups on the terminus of the tunicamycin N-acyl chains. Chemically modified TunR1-omega-X and TunR2-omega-X analogs (shown on the figure) can also be produced by catalytic hydrogenation of the corresponding tunicamycin-omega-X and are considerably less toxic to eukaryotes whilst retaining their antibacterial activities.

Moreover, chemical modification of the new omega-alicyclic tunicamycins (OATs) gives access to a large family of novel and previously unreported tunicamycin structures. For example, by selective catalytic hydrogenation with either Pt/C or $Rh/Al_2O_3$ catalyst novel TunR1-OATS or TunR2-OATS, respectively have been produced. Hence, the double bonds are selectively hydrogenated (reduced): 1. In the 2,3-trans-double bonds in the N-acyl groups of TunR1-OATS; or 2. in the 2,3-trans-double bonds in the N-acyl groups and also the uridine double bonds of TunR2-OATS.

FIG. 6A depicts a bacterial PNPT-catalyzed enzyme reaction of UDP-GlcNAc and undecaprenyl phosphate. FIG. 6B shows a schematic structure of tunicamycin, with arrows indicating the double bonds that are hydrogenated in the modified tunicamycins, TunR1 and TunR2. FIG. 6C depicts the binding interaction mediated by π-π stacking between the uridyl group of tunicamycin and Phe249[1] in the PNPT uridyl binding pocket. This specific face-to-face ring binding interaction is attenuated for TunR2 because of the 5,6-dihydrouridyl moiety of TunR2 is non-planar.

[1]The Phe249 numbering is based on the human PNPT, called hGPT.

Other small, cyclic carboxylic acids investigated as potential precursors of non-natural tunicamycins are heterocyclic types (containing N or O atoms in the ring) and cycloalkene types. Only cyclopent-3-ene (Tun-3C5ene) and cyclohex-3-ene (Tun-3C6) gave rise to new OAT-type tunicamycins. The heterocyclic carboxylates all failed to incorporate. Hence, the pathways leading to the OATs in this application are highly selective, as described.

The biological activity of the OATs has been assessed against bacterial and eukaryotic system and several have enhanced antibacterial activity against *Mycobacterium* species. We show that the OATs also block the formation of mycobacterial biofilm as a probable consequence of the inhibition of arabinogalactan formation.

Finally, the new OATs structures are highly amenable to chemical modification to give access to a large family of novel tunicamycins. As examples, the quantitative hydrogenation/reduction of double bonds in the OATs molecules gives new structures (TunR1-OATs and TunR2-OATS) that have excellent antibacterial and antimycobacterial properties and have considerably reduced eukaryotic toxicity. Hence, these are the properties required of much needed, novel mode-of-action antibiotics.

Gram-positive bacteria are bacteria that appear violet or purple after exposure to the Gram stain test. Gram-positive bacteria contains a peptidoglycan layer in the cell wall; the Gram stain binds to or is absorbed by this peptidoglycan layer such that the stain remains after a wash. Non-limiting examples of Gram-positive bacteria include *Actinomyces* sp., *Bacillus* sp., *Clavibacter* sp., *Clostridium* sp., *Corynebacterium* sp., *Enterococcus* sp., *Lactobacillus* sp., *Leifsonia* sp., *Listeria* sp., *Mycobacterium* sp., *Mycoplasma* sp., *Nocardia* sp., *Propionibacterium* sp., *Rathybacter* sp., *Staphylococcus* sp., *Streptococcus* sp., and *Streptomyces* sp. *Bacillus subtilis* strain MW10 is commonly used in experiments as an example for Gram-positive bacteria. *Escherichia coli* is commonly used in experiments as an example for Gram-negative bacteria.

The omega-alicyclic tunicamycins and related compounds of this invention can be combined with penicillin and/or other antibiotics in the penicillin family. The combination product has synergist effect of enhancing toxicity against bacteria (Gram-positive bacteria), thereby allowing less penicillin or its related antibiotics being used to kill the bacteria. The combination product can overcome the resistance to penicillin that many bacteria have developed. Non-limiting examples of penicillin antibiotics include naturally occurring penicillins (penicillin G and penicillin V), β-lactamase resistant penicillins (methicillin, nafcillin, oxacillin, cloxacillin, dicloxacillin), aminopenicillins (ampicillin, amoxicillin, pivampicillin, hetacillin, bacampicillin, metampicillin, talampicillin, epicillin), carboxypenicillins (carbenicillin, ticarcillin) and ureidopenicillins (mezlocillin, piperacillin). Other penicillins include azlocillin and flucloxacillin.

Penicillins are β-lactam antibiotics. So, the omega-alicyclic tunicamycins and related compounds can be combined with any β-lactam antibiotics and have enhanced antibacterial activity. In addition to penicillins, β-lactam antibiotics include, but are not limited to cephalosporins, monobactams (such as, aztreonam, tigemonam, nocardicin A, and tabtoxin) and carbapenems (such as, imipenem/cilastatin, meropenem, ertapenem, doripenem, panipenem, biapenem, razupenem, tebipenem, lenapenem, tomopenem, and thienamycin). Non-limiting examples of cephalosporins includes cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefuroxime, cefuzonam, cefmetazole, cefotetan, cefoxitin, cefbuperazone, cefminox, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriazoxime, ceftriaxone, cefoperazone, ceftazidime, oxacephems (including latamoxef and flomoxef), cefclidine, cefepime, cefluprenam, cefoselis, cefozopran, cefpirome, cefquinome, ceftobiprole, ceftaroline, and ceftolozane.

The omega-alicyclic tunicamycins and related compounds can be combined with antibiotics that are not β-lactam antibiotics (referred to herein as "non-β-lactam antibiotic"), including but not limited to geldanamycin, herbimycin, carbacephem, loracarbef, cefalothin, cefalexin, cefamandole, cefoxitin, cefprozil, teicoplanin, vancomycin, macrolides, azithromycin, clarithromycin, dirithromycin, erythromycin, roxithromycin, troleandomycin, telithromycin, spectinomycin, aztreonam, bacitracin, colistin, polymyxin B, quinolones, ciprofloxacin, enoxacin, gatifloxacin, levofloxacin, lomefloxacin, moxifloxacin, norfloxacin, ofloxacin, trovafloxacin, mafenide, prontosil, sulfacetamide, sulfamethizole, sulfanilimide, sulfasalazine, sulfisoxazole, trimethoprim, trimethoprim-sulfamethoxazole (TMP-SMX), demeclocycline, doxycycline, minocycline, oxytetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin or rifampicin, and/or tinidazole; to name a few. Other antibiotics known in the art that are used against Gram-positive bacteria may be added to the compositions described herein, provided they do not substantially interfere with the intended activity and efficacy of the compositions described herein. Whether or not another antibiotic interferes with activity and/or efficacy of the compositions described herein can be determined, for example, by the procedures utilized below.

As used herein an effective amount" refers to the amount of omega-alicyclic tunicamycins or related compound, or antibacterial compositions containing at least one omega-alicyclic tunicamycins or related compound (with or without other antibiotics) that, when it is administered to or on an animal, kills bacteria that live in or on the animal. Applying/administering an effective amount of at least one omega-alicyclic tunicamycins or related compound or antibacterial compositions containing at least one omega-alicyclic tunicamycins or related compound to an animal is the application/administering of that amount which is necessary to kill bacteria, prevent the growth of bacteria, to prevent a bacterial disease, to treat a bacterial disease in or on the animal being treated. An effective amount of one or more omega-alicyclic tunicamycins or related compounds (or compositions containing the omega-alicyclic tunicamycins or related compounds) to disinfect an object or surface is that amount which, when applied to the object or surface, will kill bacteria on that object or surface and/or which will prevent the growth of bacteria on that object or surface.

As used herein, the term "about" is defined as plus or minus ten percent of a recited value. For example, about 1.0 g means 0.9 g to 1.1 g.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

Embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby. All publications, patents, and patent applications mentioned in this specification are herein incorporated by reference to the same extent as if each individual publication, patent, or patent application was specifically and individually indicated to be incorporated by reference.

EXAMPLES

Having now generally described this invention, the same will be better understood by reference to certain specific examples, which are included herein only to further illustrate the invention and are not intended to limit the scope of the invention as defined by the claims.

Example 1

Preparation and Production of Omega-Alicyclic Tunicamycins (OATs)

Production of Omega-alicyclic tunicamycins (OATs).

The tunicamycin-related compounds (TUN) can be prepared by any of the methods described herein or any method known to one of skill in the art. General methods for production of tunicamycins are found in N P J Price et al., 2019, "Synergistic enhancement of beta-lactam antibiotics by modified tunicamycin analogs TunR1 and TunR2," J. Antibiot. 72(11):807-815; N P J Price et al., 2021, "Branched Chain Lipid Metabolism As a Determinant of the N-Acyl Variation of Streptomyces Natural Products," ACS Chem. Biol. 6(1):116-124.

The TUN were produced by aerobic fermentation of a TUN-producing Actinomycetes strain in liquid culture media for 6 to 10 days. Table 1 below lists examples of tunicamycin-producing Actinomycetes strains identified by genomic screening with the pathway-specific tun genes and by chemical analysis of fermentation broths. Unique to the tunicamycin biosynthetic operon are tunB gene that encodes for SAM-dependent methyltransferase homologs and tunD gene that encodes for glycosyltransferase homologs. Strains with one asterisk (*) have been confirmed to produce tunicamycins in culture by mass spectrometry (MS). Strains with two asterisk () are newly identified in this paper. Strains with three asterisk (*) are shown by MS to be non-producers. Tunicamycins (TUN), quinovosamycins (QVM), streptovirudins (STV), corynetoxins (COR).

TABLE 1

Tunicamycin-Producing Actinomycetes Strains

| Strain Designation | TUN | QVM | STV | COR |
|---|---|---|---|---|
| *Streptomyces chartreusis* NRRL 12338 | * | | | |
| *Streptomyces chartreusis* NRRL 3882 | * | | | |
| *Streptomyces lysosuperificus* ATCC 31396 | * | | | |
| *Streptomyces* sp. CB02923 | * | | | |
| *Streptomyces* sp. fd1-xmd | | | | |
| *Streptomyces amritsarensis* strain MTCC 11845 | | | | |
| *Streptomyces* sp. IMTB 1903 | | | | |
| *Streptomyces* sp. NRRL F-4474 | ** | | *** | |
| *Streptomyces niger* strain NRRL B-3857 | | * | | |
| *Streptomyces clavuligerus* strain F613-1 | | | | |
| *Streptomyces clavuligerus* NRRL 3585 (ATCC 27064) | | | | |
| *Nocardia nova* SH22a | | | | |
| *Lentzea flaviverrucosa* strain CGMCC 4.578 | | | | |
| *Actinosynnema mirum* DSM 43827 | *** | | | |
| *Actinosynnema pretiosum* strain X47 | | | | |
| *Streptomyces* sp. PCS3-D2 | | | | |
| *Streptomyces viridifaciens* strain DSM 40239 | | | | |
| *Rathayibacter iranicus* strain DSM 7484 | | | | |
| *Rathayibacter iranicus* strain FH154 RFBF1_58 | | | | |
| *Rathayibacter iranicus* strain TRS5 RFBH1_85 | | | | |
| *Pseudonocardia* sp. HH130629-09 | | | | |
| *Corynebacterium striatum* strain 216 | | | | |
| *Rathayibacter toxicus* strain FH100 | | | | *** |
| *Rathayibacter toxicus* strain WAC3373 | | | | |

The tunicamycins were cultured in tryptone:yeast extract: glucose (TYG medium) at 20° C. to 30° C. with agitation. Produced actinomycete cells and TUN were precipitated from the spent media by addition of acid (typically HCl) and recovered by filtration or centrifugation. The TUN materials were extracted from the cell pellets with methanol or other suitable extraction solvent, and subsequently recovered by evaporation of the solvent. These are referred to in the literature as naturally-occurring tunicamycins, and these occur as mixtures of several TUN compounds with different branched chain N-acyl groups (C13-18, iso- or anteiso-branched), which were separated and purified by various chromatographic procedures such as reversed phase C18 and C30 HPLC.

Omega-alicyclic tunicamycins (OATs) are produced by substrate-directed fatty acid biosynthesis using suitable biosynthetic precursors. TUN-producing Actinomycetes strains are grown in liquid TYG medium as described, and with the inclusion of small quantities of small organic carboxylic acids in the media. These acids may be present as salts (for example sodium or potassium salts) which are readily achievable by neutralization with a suitable base (carbonates, bicarbonates and hydroxides being examples). Typically, the carboxylic acid salts are dissolved in TYG medium at a concentration range of 10-200 mg/100 mL, and optimally at 50 mg/100 mL. Quantities greater than 200 mg/100 mL were detrimental to the growth of the Actinomycetes and lower that 10 mg/mL resulted in insufficient yields of the OATs.

At the termination of the aerobic fermentation growth (typically 10 days) the OATs are recovered from the spent media, for example by acid precipitation and methanol extraction. *Streptomyces chartreusis* NRRL 12338 or *Streptomyces chartreusis* NRRL 3882 are preferred fermentation strains for the production of OATs, although other tunicamycin producing stains are also suitable (for other examples see Table 1: *Streptomyces clavuligerus* NRRL 3585, ATCC 27064, *Streptomyces lysosuperificus* ATCC 31396 for the production of OATs, *Streptomyces* sp. F4474 for production of OATs and/or omega-alicylic streptovirudins (OASs), and *Streptomyces niger* strain NRRL B-3857 for productions of OATs and/or omega-alicylic quinovosamycins (OAQs). In general, mixtures of OATs (or OASs or OAQs) are obtained from the fermentations and are readily characterized and quantified by a combination of HPLC, LC-MS, and matrix assisted laser desorption/ionization mass spectrometry (MALDI-MS) techniques as described.

Chemical structures of omega-alicyclic tunicamycins (OATs) examples are shown in FIG. 7A to FIG. 7C, which show examples of C5C tunicamycins, C6C tunicamycins, and 6C3ene tunicamycins. FIG. 7A depicts the structure of tunicamycin Tun 16:1-C5C and tunicamycin Tun-14:1-C5C. FIG. 7B depicts the structure of tunicamycin Tun-17:1-C6C and tunicamycin Tun-15:1-C6C. FIG. 7C depicts the structure of tunicamycin Tun-17:1-6C3ene and tunicamycin Tun-15:1-6C3ene.

OATs and the natural tunicamycin are produced together in the fermentations, and individual components need to be purified by reverse-phase HPLC. The individual peaks are detected using a diode-array detector (DAD) and are collected either manually or with a fraction collector. The less hydrophobic components which have shorter N-acyl chains elute earliest. Longer chain-length, more hydrophobic components elute later. The novel OATs produced are easily identified (arrowed in red in FIG. 8A to FIG. 8F) by running a standard of the natural tunicamycin as a background control. Hence, all of the OATs shown in FIG. 8A to FIG. 8F were identified and purified by reverse-phase HPLC in this way. Native tunicamycins (control) and omega-alicyclic tunicamycins from *S. chartreusis* NRRL 12338 were analyzed by RP-C30-HPLC, and the results are shown in FIG. 8A to FIG. 8F, with the mass assignments done by MALDI-TOF-MS. FIG. 8A depicts a graph of the native tunicamycins obtained. FIG. 8B depicts a graph of tunicamycins prepared using C5C primer, with the new omega-alicyclic tunicamycins formed indicated with arrows and letters (A: Tun-16:1-C5C; B: Tun-16:0-C5C; C: Tun-18:1-C5C). FIG. 8C depicts a graph of tunicamycins prepared using C4C primer, with the new omega-alicyclic tunicamycins formed (Tun 15:1-C4C and Tun-17:1-C4C) indicated with arrows. FIG. 8D depicts a graph of tunicamycins prepared using C6C primer, with the new omega-alicyclic tunicamycins formed (Tun-15:1-C6C; Tun-15:1-C6C; and Tun-17:1-C6C) indicated with arrows. FIG. 8E depicts a graph of tunicamycins prepared using 3C5ene primer, with the new omega-alicyclic tunicamycins formed (Tun-16:1-3C5ene; and Tun-18:1-3C5ene) indicated with arrows. FIG. 8F depicts a graph of tunicamycins prepared using 3C6ene primer, with the new omega-alicyclic tunicamycins formed (TTun-13:1-3C6-ene; Tun-15:1-3C6-ene; Tun-15:0-3C6-ene; and Tun-17:1-3C6-ene) indicated with arrows.

The information given in this example shows examples of the new omega-alicyclic tunicamycins formed using the methods of the invention.

Example 2

Structural Characterization of OATs

Reversed-phase HPLC and mass spectrometry techniques (MALDI-TOF/MS, positive ion- and negative ion-detected LC/ESI/MS) were used as verification of the chemical structures of the claimed OATs.

A rapid and useful way to characterize OATs and tunicamycins is the use of MALDI-TOF mass spectrometry. The molecular masses obtained were as [M+Na]$^+$ ions and were typically in the 700-1000 Da mass range. Individual compounds typically differed by 14 Da, which is the mass of $CH_2$, so that an increased mass of 14 Da corresponds to a chain length of one —$CH_2$—. Examples of this are molecular masses m/z 839, 853, 867, 881 which corresponded to the natural tunicamycins Tun-14:1, Tun-15:1, Tun-16:1, and Tun-17:1. Hence, novel MALDI-MS molecular mass ions are characteristic of the new OATs compounds—for example, m/z 879 for Tun-17:1-C4C and Tun-17:1-C6C, m/z 865 for Tun-16:1-CSC, and m/z 893 for Tun-18:1-C7C. Moreover, the relative quantitative production of these new OATs compounds was assessed by MALDI-MS by comparison with a known internal standard of a natural tunicamycin such as Tun16:1 (m/z 867) using the ion peak intensities either as peak heights or peak area. Hence, as seen in FIG. 9A to FIG. 9F, the novel OATs Tun-17:1-C4C (FIG. 9B), Tun-16:1-C5C (FIG. 9C), Tun-18:1-C5C (FIG. 9D), Tun-17:1-C6C (FIG. 9E), and Tun-18:1-C7C (FIG. 9F) are found in the ratio 0.13:0.9:0.42:8:93:0.11 relative to Tun-16:1. It is noteworthy that this shows the new OAT Tun-17:1-C6C is produced in fermentation at 8.93-times larger amounts than the Tun16:1 internal control.

Cycloalkene-type OATs (3C6eneCA, 3C6eneCA, 1C5eneCA, 3C5eneCA, and 3C5eneCA) are similarly characterized by MALDI-MS molecular masses m/z 877, m/z 905, m/z 891, and m/z 863, and m/z 891, respectively, and are shown in FIG. 9G to FIG. 9L. Similarly, these are quantified in the fermentations relative to Tun-16:1 as being in the ratio 1.29:0.12:0.17:0.48:0.10.

Further characterization the OATs, both cycloalkane- and cycloalkene-types, was achieved by liquid chromatography-electrospray ionization-mass spectrometry (LC/ESI/MS). This has the advantage of giving molecular ions (either positive charged [M+H]$^+$ and [M+Na]$^+$, or negative charged [M−H]$^-$) plus certain fragment ions (M-220) that are characteristic of the tunicamycins. The LC/ESI/MS +ve ions of omega-alicyclic 5C5 tunicamycins A, B, and C from *S. chartreusis* NRRL 12338 grown on TYG plus C5C primer are shown in FIG. 10A. Note the correlations with the [M+Na]$^+$ ions observed by MALDI-TOF MS (m/z 865, 867, and 893). Note the [M+H−221]$^+$ fragment ions at m/z 622, 624, and 650 which are characterized for tunicamycins. The LC/ESI/MS with −ion detection for characterization of example OATs Tun16:1-C5C, Tun16:0-C5C, and Tun18:1-C5C, corresponding to the MS +ve ions shown in FIG. 10A are shown in FIG. 10B.

Negatively charged ions ([M−H]$^-$ were obtained at m/z 841.1 (Peak A), 843.1 (Peak B), and 869.2 (Peak C) are assigned as the example OATs Tun16:1-C5C, Tun16:0-C5C, and Tun18:1-C5C (FIG. 10B). Note that these correspond with the positively charged ions [M+H]$^+$ obtained (m/z 843, 845, and 871) (FIG. 10A). Hence, the LC/ESI/MS data are characteristic of and fully consistent with the claimed OATs structures.

Example 3

NMR Characterization of OATs

Nuclear magnetic resonance techniques ($^1$H-NMR and $^{13}$C-NMR spectra and two-dimensional HSQC, COSY, HMBC and DEPT NMR) were used as verification of the chemical structures of the claimed OATs.

The gold standard technique for structural characterization of novel organic molecules is nuclear magnetic resonance (NMR) spectroscopy. The complete NMR assignments for the naturally occurring tunicamycins, and quinovosamycins has been published, as have the assignments for tunicamycins made by chemical synthesis. Essentially the tunicamycin molecules are comprised of four separate NMR spin systems (labeled A, B, C and D in FIG. 11), connected via N or O heteroatoms. The systems A, B and D are structurally conserved in all tunicamycins (except for quinovosamycins, where A is a QuiNAc sugar residue rather than the GlcNAc shown in FIG. 11). This core structure called tunicaminyl-uracil is also present in the new OATs molecules in this report. However, spin system C corresponds to the tunicamycin N-acyl chain, and this is more variable, both in the $CH_2$ chain length (n, typically 7-11) and in the identity of the omega position X group at the end of the chain. For OATs this X group is novel and composed of a cycloalkane or cycloalkene ring, whereas for the natural tunicamycins the omega group is an iso-branched —$CH(CH_3)_2$ or anteiso-branched —$CH(CH_3)(CH_2CH_3)$ group. Because of this, the NMR spectra of the described OATs are very distinct from the natural tunicamycins for spin system C, in particular for the NMR signals arising from the omega X group at the terminal position.

One dimensional $^1$H-NMR and $^{13}$C-NMR spectra and two-dimensional HSQC, COSY, HMBC and DEPT NMR spectra were acquired for all of the OATs molecules reported. The most characteristic proton and carbon assignments are evident from comparative HSQC and DEPT spectra, and these are reproduced in FIG. 12A to FIG. 12E. The HSQC and DEPT NMR data for 3-C5-ene OAT is shown in FIG. 12A, where the left panel presents data for 0 to 8 ppm, center panel presents data for 2.8 to 4.5 ppm, and the right panel presents data for 0 to 2.5 ppm. The HSQC and DEPT NMR data for 3-C6-ene OAT is shown in FIG. 12B, where the left panel presents data for 0 to 8 ppm, center panel presents data for 2.8 to 4.5 ppm, and the right panel presents data for 0 to 2.5 ppm. The HSQC and DEPT NMR data for C5-TunR1 OAT is shown in FIG. 12C, where the left panel presents data for 0 to 8 ppm, center panel presents data for 2.8 to 4.5 ppm, and the right panel presents data for 0 to 2.5 ppm. The HSQC and DEPT NMR data for C6-TunR1 OAT is shown in FIG. 12D, where the left panel presents data for 0 to 8 ppm, center panel presents data for 2.8 to 4.5 ppm, and the right panel presents data for 0 to 2.5 ppm. FIG. 12E on the left panel shows data for C5-TunR2 OAT 0.8 to 6.0 ppm; on the center panel shows data for C6C-TunR2 Oat, 0.7 to 6.0 ppm; and on the left panel shows data for C6C-TunR2 0.4 to 2.2 ppm. Numbering refers to the assignments in Table 2 below, where the 13-carbon chemical shifts are listed first, followed by proton chemical shifts. A hashtag symbol (#) indicates alicyclic ring positional numbering at the end of the N-acyl-chain.

TABLE 2

$^1$H- and $^{13}$C-NMR chemical shifts* (ppm) of ω-alicyclic tunicamycins

|  |  | Tun-C5C | TunC5C-3-ene | Tun-C6C | Tun-C6C-3-ene |
|---|---|---|---|---|---|
| uridyl ring | 5 | 103.1; 5.89 | 101.6; 5.77 | 103.1; 5.89 | 101.5; 5.76 |
|  | 6 | 142.8; 8.05 | 141.8; 7.95 | 142.6; 8.07 | 141.2; 7.92 |
| tunicamine ring | 1' | 89.9; 6.05 | 90.0; 6.03 | 89.9; 6.04 | 88.3; 5.92 |
|  | 11' | 102.0; 4.71 | 102.0; 4.62 | 102.0; 4.73 | 102.0; 4.71 |
| GlcNAc ring | 1" | 100.3; 5.04 | 100.1; 5.08 | 100.6; 5.10 | 100.3; 4.92 |
| N-acyl chain | 1''' | 169.7 | 169.7 | 169.6 | 169.7 |
|  | 2''' | 124.9; 6.07 | 123.4; 6.00 | 124.7; 6.06 | 123.5; 6.07 |
|  | 3''' | 146.5; 6.94 | 144.5; 6.82 | 146.8; 6.98 | 144.9; 6.82 |
|  | 4''' | 33.0; 2.32 | 33.0; 2.32 | 33.0; 2.30 | 33.0; 2.34 |
| ω-alicyclic ring positions | 1# | 40.6; 1.41 | 41.1; 1.80 | 29.4; 1.50 | 34.5; 1.55 |
|  | 2# | 32.8; 1.90, 1.65 | 41.2; 2.02, 1.77 | 33.6; 1.63, 1.38 | 36.4; 2.19, 1.84 |
|  | 3# | 25.1; 1.73, 1.63 | 129.4; 5.60 | 25.8; 1.53, 1.43 | 126.0; 5.65 |
|  | 4# | 25.1; 1.73, 1.62 | 129.3; 5.61 | 26.0; 1.46, 1.44 | 126.0; 5.66 |
|  | 5# | 32.8; 1.90, 1.65 | 41.2; 2.02, 1.77 | 25.8; 1.54, 1.43 | 23.1; 2.11, 2.01 |
|  | 6# |  |  | 33.6; 1.63, 1.38 | 29.3; 1.59, 1.34 |

The $^1$H-NMR, $^{13}$C-NMR and 2D NMR spectra shown are fully consistent with the claimed OATs structures. Key features are the α1" and β-11' anomeric signals due to the tunicaminyl 1"-11' glycosidic linkage of GlcNAc to tunicamine-uracil (these are at C1" 100.3/H1" 5.0 ppm; C11' 102.0/H11' 4.7 ppm, respectively), and the uridyl double bond signals (at C5 103.1/H5 5.9 ppm; C6 142.8/H6 8.0 ppm). The latter signals (H5/C5 and H6/C6) disappear from the spectra when the uridyl double bond is chemically hydrogenated (reduced), as it is in TunR2-type OATs (FIG. 12E. left panel). Similarly, the double bond in the N-acyl chains is apparent from signals at C2''' 124.9/H2''' 6.1 ppm and C3''' 146.5/H3''' 6.9 ppm, and these also disappear as expected when the N-acyl double bond is hydrogenated, as it is in the TunR1- and TunR2-type OATS (as shown in the left panels of FIG. 12D and FIG. 12E, respectively). Other NMR assignments are characteristic of the expected GlcNAc-tunicaminyl ring protons (3.2-4.3 ppm) and ring carbons (50-90 ppm) (FIGS. 12A-E). Other important NMR assignments for the OATs are due the ω-alicyclic groups (FIGS. 12A-E, right panels), and for the ω-alicyclic-3-ene-type OATs (for example, OAT-C5C-3-ene and OAT-C6C-3-ene) are the 3-ene double bond signals (FIG. 12A and FIG. 12B left panels, respectively. As expected, these 3-ene NMR signals are also lost following hydrogenation to the corresponding TunR1- and TunR2-type OATs, as shown below.

Example 4

Chemical Hydrogenation of OATs to Less Toxic TunR1- and TunR2-Type OATS

The claimed OATs were catalytically hydrogenated (reduced) to produce TunR1- and TunR2-type OATs on a quantitative basis, and all of these have been structurally verified. Some of TunR1- and TunR2-type OATs are shown to have enhanced antimycobacterial activity and reduced toxicity against eukaryotes.

Catalytic hydrogenations may quantitatively convert the OATs described above into TunR1-type OATs and TunR2-type OATs. Using MALDI-MS, LC/MS, and NMR these new compounds have been characterized, and their reduced toxicity in bioassays with eukaryotes with retention of their potent antibacterial activity is shown below.

MALDI-TOF mass spectrometric evidence for the quantitative hydrogenation of Tun-C6C type omega-alicyclic tunicamycins (OATs) into the corresponding TunR1 and TunR2 OATs analogs is shown in FIG. 13. For example, the major C6C OATs, Tun-17:1-C6C (m/z 879.642) is reduced with $H_2$/Pt to TunR1-17:0-C6C (m/z 881.549), and with $H_2$/Rh to give TunR2-17:0-C6C (m/z 883.772). The reduced double bonds results in the expected mass increases of 2 Da or 4 Da as shown.

Double bonds are present in the claimed OATs at position 5,6 in the uracil ring and at position 2''',3''' in the N-acyl group. We have previously shown that these double bonds can be selectively reduced to single bonds by catalytic hydrogenation. Hence, the N-acyl double bond can be reduced with hydrogen gas over platinum on carbon (Pt/C) or palladium on carbon (Pd/C) catalysts to give compounds that we have named OAT-TunR1 (Tunicamycins Reduction 1). Alternatively, the N-acyl double bond and the uracil double bond can both be reduced together in a single reaction using rhodium on alumina catalyst ($Rh/Al_2O_3$) to give compounds we have named OAT-TunR2 (Tunicamycins Reduction 2). The reduction may also be accomplished by a variety of other methods as described and discussed in our prior patent [Price, US 2018/0208620]. The progress of these reduction reaction is monitored by MALDI-TOF mass spectrometry, hence reduction of one double bond leads to an increase of molecular mass by 2 Da, and reduction of both double bonds increases the mass by 4 Da.

As examples, the major omega-cyclohexyl-type C6C-OAT-17:1 with molecular masses m/z 879.642 is reduced with $H_2$/Pt to OAT-TunR1-17:0-C6C (m/z 881.549), and with $H_2$/Rh to give TunR2-17:0-C6C (m/z 883.772) are shown in FIG. 13. The hydrogenation is quantitative, and the completion of reaction is evident from the product ions and the disappearance of MS ions for the starting material. The omega-cyclohexyl-type OATs is shown as an example, but the hydrogenation reactions are equally applicable to all of the new OATs. We also note that the hydrogenations may be accomplished on mixtures of OATs followed by purification by reversed phase HPLC, or the OATs may be pre-purified by said chromatography followed by the catalytic hydrogenation steps. The biological importance of the claimed TunR1-type OATs and TunR2-type OATs is evident from their greatly reduced eukaryotic toxicity relative to the corresponding non-modified OATs or to the corresponding tunicamycins (see section below).

In this section all of the claimed OATs produced by the fermentation described were catalytically hydrogenated on a quantitative basis to produce the corresponding TunR1- and TunR2-type OATs. These were all structurally verified by mass spectrometry and nuclear magnetic resonance spectroscopy. Some of which have enhanced antimycobacterial activity and reduced toxicity against eukaryotes, as described below.

Example 5

OAT Bioactivities

The biological activities of the claimed OATs, TunR1-type OATs and TunR2-type OATs produced by the methods described above were tested against a Gram-positive bacterium (*Bacillus subtilis*), *Mycobacterium* strains including pathogenic *Mycobacterium avium* subsp. *paratuberculosis*, and against *Saccharomyces cerevisiae* (yeast) as a model eukaryote.

The biological activities of the claimed OATs, TunR1-type OATs and TunR2-type OATs was tested against a Gram-positive bacterium (*Bacillus subtilis*) and as a model eukaryote *Saccharomyces cerevisiae* (yeast). These assays were done using standard microbiological methods, for example by spotting dilutions of the Tun compounds on solid agar media plates after inoculating with bacteria or yeast and incubating for a defined period. This method results in clearing zones on agar plates. Noticeably, the C6C-OAT (FIG. 14, spot 3 is highly toxic to both *Bacillus* and yeast, with a toxicity similar to commercial tunicamycin (spot 1). However, the hydrogenated TunR2-type compound, C6C-TunR2-OAT (spot 5) is considerably less toxic to the yeast while retaining its potent activity against the *Bacillus*. Hence, TunR1-type and TunR2-type OATs have potential as less toxic and novel mode-of-action antibacterial agents.

As further examples of the antibiotic activities of the OATs the relative biological activities against *Mycobacterium* species was investigated. *Mycobacterium* is a genus of Actinobacteria that includes several pathogens known to cause serious diseases in mammals, including tuberculosis (*Mycobacterium tuberculosis*) and leprosy (*Mycobacterium leprae*) in humans, and Johne's disease in sheep and cattle (*Mycobacterium avium* subsp. *paratuberculosis*). Multi-drug resistant strains from this genus have emerged and therefore, new drugs to treat these diseases are of considerable importance.

Shown in FIG. 15C are the relative bioactivities of tunicamycin and OATs, C5C-Tun, C5C-TunR1, and C5C-TunR2, on *Mycobacterium smegmatis* (LEFT and CENTER), a model organism for *M. tuberculosis*, and against *Mycobacterium avium* subsp. *paratuberculosis* (RIGHT), the pathogenic agent of Johne's disease in livestock. The TunR2 anti-*Mycobacterium* activity is arrowed.

The relative biological activities of the claimed OATs, TunR1-type OATs and TunR2-types OATs were initially tested against *Mycobacterium smegmatis*, which is a commonly used non-pathogenic model organism for the far more lethal *M. tuberculosis* (N Lelovic et al, 2020, "Application of *Mycobacterium smegmatis* as a surrogate to evaluate drug leads against *Mycobacterium tuberculosis*," J. Antibiotics 73: 780-789). As seen in FIG. 15A, C5C-TunR2 (spot 6) presented with a very good activity, better than commercial tunicamycin, against *Mycobacterium smegmatis*, whereas this compound was non-toxic against the eukaryotic yeast cells. This shows the therapeutic potential of the modified TunR2-type OATs as novel anti-mycobacterial agents which are also safe to use in the host.

This was further evaluated using a pathogenic strain of *Mycobacterium avium* subsp. *paratuberculosis* (MAP), the causative agent of Johne's disease in livestock, and the results are shown in FIG. 15C. MAP strain K-10 used in the study is a slow growing *Mycobacterium*. Agar plates were first inoculated with cotton swabs dipped in broth culture and grown for 17 days. The antibiotic discs were applied 4 days after inoculation and thus were on the plate for 13 days. The MAP strain K-10 is resistant to various commonly used antibiotics (sterulic acid, thiocarlide, imipenem, carbenicillin, and cefquinome). The tunicamycins, however, perform well on the MAP strain K-10, including TunR1 and TunR2 activities (arrowed in FIG. 15B). Carbenicillin and cefquinome have low inhibitions at high concentrations, but the rest of the antibiotics are ineffective. The inventors therefore concluded that the modified TunR2-type compounds have potential as novel mode of action anti-mycobacterial agents.

The inventors have shown that tunicamycins (including the modified TunR1, TunR2, and OAT-type tunicamycins) have potent antimycobacterial activity (for example, MIC 0.5 µg·mL$^{-1}$ for TunR2 against *M. smegmatis*, as shown in FIG. 16.

Tunicamycins are known to inhibit the biosynthesis of bacterial cell wall, for example by blocking the peptidoglycan and teichoic layers. The *Mycobacterium* genus is characterized by unusual and complex cell walls composed of three distinct layers, peptidoglycan (PG), arabinogalactan (AG) and mycolic acids (MA), which are well characterized targets for antimycobacterial drugs (K A Abrahams & G S Besra, 2018, "Mycobacterial cell wall biosynthesis: a multifaceted antibiotic target," Parasitology 145: 116-133). The MA and AG are also components of mycobacterial biofilms, an extracellular matrix with various pathogenic functions. As seen in FIG. 16, tunicamycins (including the less-toxic TunR2-type compounds) are both antimycobacterial and potent inhibitor of biofilm formation (Minimal Biofilm Formation Concentration, MBFC=0.25 µg·mL$^{-1}$). This is evident in a microtiter plate bioassay that shows growing mycobacterial cells in clear wells and biofilms as turbidity in FIG. 16.

Without wishing to be bound by theory, the inventors propose here a mechanism for this anti-biofilm activity of tunicamycins via inhibition of the mycobacterial arabinogalactan (AG) layer. The biosynthesis of AG understood, and is initiated on a prenol carrier, decaprenyl phosphate (C50-P), on which the cell wall linker unit (Rha-GlcNAc-P-) is constructed. The first steps are catalyzed by the membrane-bound enzymes GlcNAc-1-phosphate transferase WecA and rhamnosyltransferase WbbL giving rise to AG intermediates known as GL1 (C50-P-P-GlcNAc) and GL2 (C50-P-P-GlcNAc-Rha) [Abrahams & Besra, 2018]. WecA is a member of the MraY family of enzymes (see FIG. 2) and is a well-defined target for inhibition by tunicamycins, resulting in mis-assembly of the AG layer. FIG. 16 shows that this results in mycobacterial cell death and biofilm inhibition. It is also shown, that modified tunicamycins, such as TunR2-type, are more potent inhibitors of mycobacterial growth (MIC=0.5 µg·mL$^{-1}$) and of biofilm formation (MBFC=0.25 µg·mL$^{-1}$) than are native tunicamycins (2 and 1 µg·mL$^{-1}$, respectively), while at the same time have considerably reduced eukaryotic toxicity (FIG. 16).

In Example 5, the biological activities of the OATs, TunR1-type OATs and TunR2-type OATs produced by the methods described above were tested against a Gram-positive bacterium (*Bacillus subtilis*), *Mycobacterium* strains including pathogenic *Mycobacterium avium* subsp. *paratuberculosis*, and against *Saccharomyces cerevisiae* (yeast) as a model eukaryote. All were shown to have good antibacterial activity against Gram-positive bacteria. TunR1-type OATs and TunR2-type OATs were shown to be considerably less toxic to a model eukaryote (yeast) while retaining its potent antibacterial activity. TunR2-type compounds are shown to be excellent antimycobacterial agents ((MIC=0.5 µg·mL$^{-1}$) and potent inhibitor of biofilm formation (Minimal Biofilm Formation Concentration, MBFC=0.25 µg·mL$^{-1}$). The inventors propose a mechanism for the observed anti-mycobacterial activities wherein OATs, TunR1-type OATs and TunR2-type OATs inhibit mycobacterial WecA enzymes, which are members of the MraY family of enzymes and is a well-defined target for inhibition by tunicamycins (see FIG. 2), thereby resulting in mis-assembly of the mycobacterial AG cell wall layer. FIG. 16 shows that this results in mycobacterial cell death and biofilm inhibition. Hence, the modified TunR2-type materials have potential as novel mode of action anti-mycobacterial agents Example 6

Chemical Modifications of OATs

The described cycloalkene-type OATs with a double bond in the omega-cycloalkene ring may be chemically modified by a large variety of double bond (alkene) chemistries to gives access to a very large group of modified OATs with functional groups inserted into the omega-ring. This was accomplished, as an example, by the bromination of Tun-C6C-3-ene with N-bromosuccinamide in methanol to produce the substituted OAT compound 4-bromo-Tun-C6C, and this product was verified by reversed-phase HPLC purification and MALDI-TOF/MS characterization.

A major advantage of the claimed cycloalkene-type OATs is the presence of the double bond in the omega-cycloalkene ring. This can be chemically modified by a large variety of double bond (alkene) chemistries to gives access to a very large group of modified OATs with functional groups inserted into the omega-ring. Alkenes react in many addition reactions, which follow the mechanism of electrophilic addition. Common examples are hydrohalogenation, halogenation, halohydrin formation, oxymercuration, hydroboration, dichlorocarbene addition, Simmons-Smith reaction, catalytic hydrogenation, epoxidation, radical polymerization and hydroxylation. Not limiting to just these, the electrophilic halogenation is the addition of elemental bromine or chlorine to alkenes to yields vicinal dibromo- and dichloroalkanes (1,2-dihalides or ethylene dihalides), respectively. An example is —CH═CH—+Br$_2$→—CHBr—CHBr. Halogen groups introduced in this way may be converted to azide (—N$_3$) by suitable methods (for example, treatment with azide salts), and these may be subsequently reduced to amine groups for example by the Staudinger reduction. The amine groups introduced in this way may be further modified with carboxylic functions to give a large group of amides, including the introduction of fluorescent, colored, biotin or other functional groups. These chemistries will allow considerable structural diversity to be introduced into the omega-cycloalkene-type OATs. Additional biological activities and functions are expected for these new OAT-based compounds. For example, W Sittiwong et al. (US Patent Application Publication No. 2015/0175519, published Jun. 25, 2015) teach methods that may be used to modify the omega-tunicamycins of the invention.

Bromo addition across the 3-ene double bond in the alicyclic ring of Tun-C6C-3-ene. The Tun-C6C-3-ene was brominated with N-bromosuccinamide in methanol to produce substituted compound 4-bromo-Tun-C6C. which was then purified by reverse phase HPLC. Fractions were collected and assayed by MALDI TOF/MS. Fraction 7 contains m/z 979.59 which is the monobromo product 4-bromo-Tun-C6C. A graph of the reverse phase HPLC trace of the brominated tunicamycin is shown in FIG. 17A, and MALDI-TOF/MS analysis at m/z 979.59 of fraction 7 from FIG. 17A is shown in FIG. 17B.

We claim:
1. An N-acyl-tunicamycin variant of

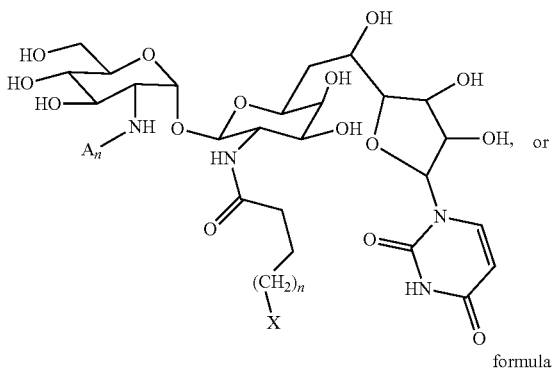

formula 1

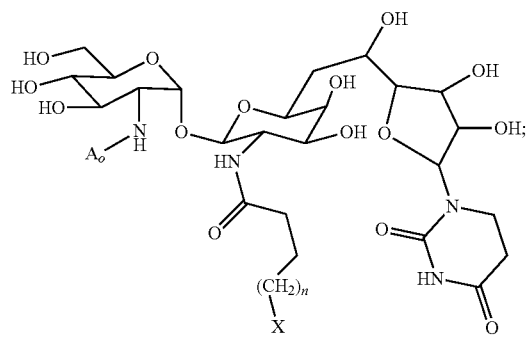

formula 2 wherein n is independently any integer from 7 to 13; and
X is a tert-butyl-branched chain, a cyclopropane, a cyclobutane, a cyclopentane, a cyclohexane, a cycloheptane, an unsaturated cyclohexene, or an unsaturated cyclopentene.

2. An antibacterial composition comprising at least one N-acyl-tunicamycin variant of claim 1.

3. The antibacterial composition of claim 2, further comprising an antibiotic, wherein said antibiotic is a β-lactam antibiotic, a non-β-lactam antibiotic, or combination thereof.

4. A method of killing Gram-positive bacteria in or on an animal comprising administering to an animal in need thereof an effective amount of the antibacterial composition of claim 2.

5. A method of killing Gram-positive bacteria in or on an animal comprising administering to an animal in need thereof an effective amount of the antibacterial composition of claim 3.

6. A method of disinfecting an object or a surface that has Gram-positive bacteria, the method comprising applying an effective amount of the N-acyl-tunicamycin variant of claim 1 to the object or the surface in order to kill the Gram-positive bacteria present on the object or the surface.

7. A method for preparing an N-acyl-tunicamycin variant of claim 1, the method comprising fermenting under aerobic conditions a tunicamycin (TUN)-producing Actinomycetes strain in liquid culture in the presence of small organic carboxylic acids.

8. The N-acyl-tunicamycin variant of claim 1, wherein the N-acyl-tunicamycin variant has antibacterial activity and blocks mycobacterial biofilm formation, wherein the bacteria is Gram-positive.

9. An N-acyl-tunicamycin variant of formula 2

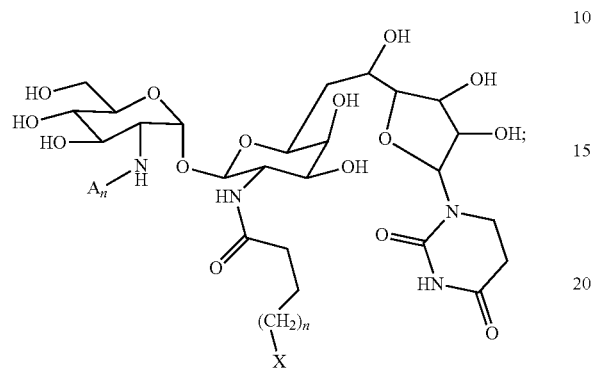

wherein n is independently any integer from 7 to 13; and

X is a tert-butyl-branched chain, a cyclopropane, a cyclobutane, a cyclopentane, a cyclohexane, a cycloheptane, an unsaturated cyclohexene, or an unsaturated cyclopentene.

10. The N-acyl-tunicamycin variant of claim 1, wherein X is an unsaturated cyclohexene or cyclopentene.

* * * * *